(12) United States Patent
Hatada et al.

(10) Patent No.: US 6,689,874 B2
(45) Date of Patent: *Feb. 10, 2004

(54) GENE FOR ENZYME HAVING BOTH ALKALINE PULLULANASE AND ALKALINE ALPHA-AMYLASE ACTIVITIES

(75) Inventors: Yuji Hatada, Tochigi (JP); Kazuaki Igarashi, Tochigi (JP); Katsuya Ozaki, Tochigi (JP); Katsutoshi Ara, Tochigi (JP); Shuji Kawai, Tochigi (JP); Susumu Ito, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/014,436

(22) Filed: Dec. 14, 2001

(65) Prior Publication Data

US 2002/0182699 A1 Dec. 5, 2002

Related U.S. Application Data

(62) Division of application No. 09/514,302, filed on Feb. 28, 2000, now Pat. No. 6,338,959, which is a division of application No. 08/952,084, filed as application No. PCT/JP96/01243 on May 10, 1996, now abandoned.

(30) Foreign Application Priority Data

May 10, 1995 (JP) .............................. 7-111547

(51) Int. Cl.⁷ ........................ C07H 21/04; C12N 9/24; C12N 9/28; C12N 9/44
(52) U.S. Cl. .................... 536/23.2; 435/200; 435/202; 435/210
(58) Field of Search .................. 536/23.2; 435/200, 435/202, 210

(56) References Cited

U.S. PATENT DOCUMENTS

5,147,796 A    9/1992  Ara et al. .................... 435/210

FOREIGN PATENT DOCUMENTS

EP    04 18835 A1    3/1991
WO    94 19468 A1    9/1994

OTHER PUBLICATIONS

Lee et al., Applied and Environmental Microbiology, vol. 60, pp. 3764–3773 (1994).
DMBL Database, EMPRO:MSP207 AAM; Accession No. X55799 (Apr. 1993).
Ara et al., Biochimica et Biophysics Acta, vol. 1243, pp. 315–324 (1995).
Kim et al., Eur.J. Biochem, vol. 227, pp. 687–693 (1995).
Saha et al., *Enzyme Microb. Technol.*, vol. 11, pp. 760–764 (1989).

*Primary Examiner*—Elizabeth Slobodyansky
(74) *Attorney, Agent, or Firm*—Birch, Stewart, Kolasch & Birch, LLP

(57) ABSTRACT

The present invention provides: a nucleotide sequence encoding alkaline pullulanase and exhibiting both alkaline α-amylase and alkaline pullulanase activity; a nucleotide sequence encoding alkaline α-amylase possessing an amino acid sequence described in SEQ ID NO:3; a nucleotide sequence encoding alkaline pullulanase possessing an amino acid sequence described in SEQ ID NO:4; recombinant DNAs containing these nucleotide sequences, and transformed microorganisms harboring the recombinant DNAs. The technique of the present invention enables mass production of alkaline pullulanase exhibiting both alkaline α-amylase and alkaline pullulanase activity.

2 Claims, 6 Drawing Sheets

```
primer 1   CTGCAGGTAT  CGGTAAATAC  GGTG
primer 2   TGACGTAACG  AATCTTGCTC  TAGA
primer 3   TCTAGAGCAT  TATCAAAAAT  TACT
primer 4   CCGGAACTGA  GAATCAAAGA  ATTC
primer 5   GAATTCGGAA  ATCGCCATGA  GGGA
primer 6   GTGGATGGTA  ATGAAATTCT  AGA
primer A   TCTAGATGTG  CAATTTTGCG  CAAAC
primer B   AAGCTTGGGG  CAGAATTGCA  TGAAG
```

FIG.6

SEQUENCE LISTING

<160> NUMBER OF SEQ ID NOS: 14

<210> SEQ ID NO 1
<211> LENGTH: 6142
<212> TYPE: DNA
<213> ORGANISM: Bacillus sp.
<220> FEATURE:
<221> NAME/KEY: CDS
<222> LOCATION: (145)..(5958)
<223> OTHER INFORMATION:
<220> FEATURE:
<221> NAME/KEY: sig_peptide
<222> LOCATION: (145)..(240)
<223> OTHER INFORMATION:
<220> FEATURE:
<221> NAME/KEY: mat_peptide
<222> LOCATION: (241)..()
<223> OTHER INFORMATION:

<400> SEQUENCE: 1

```
tctagatgtg caattttgcg caaacgattt cacatttaca taaacaatct tggcatcaat      60
taaattattt attgtgcaac tttgtgcaaa cgcttccaca ttttagcaag aaatgcaaat     120
cattgtatgg aaaggggcag ggat atg aag aaa agg ttt caa agg ggt atg        171
                           Met Lys Lys Arg Phe Gln Arg Gly Met
                               -30                     -25 gct ggt tta ctt tct att tta ctt att gtt tcc atg ttt gca ggc tat       219
Ala Gly Leu Leu Ser Ile Leu Leu Ile Val Ser Met Phe Ala Gly Tyr
            -20                 -15                 -10 cta ccg gca aga gca gcg gcc gaa acg gga gac aag cgg ata gaa ttc       267
Leu Pro Ala Arg Ala Ala Ala Glu Thr Gly Asp Lys Arg Ile Glu Phe
         -5              -1  1               5 agt tat gaa cgg cca gat gga aat tat gaa ggc tgg aat tta tgg gtc       315
Ser Tyr Glu Arg Pro Asp Gly Asn Tyr Glu Gly Trp Asn Leu Trp Val
 10              15              20              25 tgg gga act ggt gtg aag gat gac cag ata gac ttt aca gaa ttc aag       363
Trp Gly Thr Gly Val Lys Asp Asp Gln Ile Asp Phe Thr Glu Phe Lys
                 30              35              40 gaa ggc aag gca tat gcc gac ata gca gta agc gat aat gcg gat aaa       411
Glu Gly Lys Ala Tyr Ala Asp Ile Ala Val Ser Asp Asn Ala Asp Lys
             45              50              55 gtc ggt ttc att atc cgt aaa ggg gat tgg gaa gaa aag gac ttt gat       459
Val Gly Phe Ile Ile Arg Lys Gly Asp Trp Glu Glu Lys Asp Phe Asp
         60              65              70 ggg gac agg tcg att acg atc aat aag atc gat aac atc acc aaa gtg       507
Gly Asp Arg Ser Ile Thr Ile Asn Lys Ile Asp Asn Ile Thr Lys Val
 75              80              85 cat gta aca agc cag cag gaa aaa ttc ggg caa att cct gac ggc agc       555
His Val Thr Ser Gln Gln Glu Lys Phe Gly Gln Ile Pro Asp Gly Ser
 90              95             100             105 cca cct gtt gtt gcg gac ggg aat gct gac ttc ttt ttc cgt gat aaa       603
Pro Pro Val Val Ala Asp Gly Asn Ala Asp Phe Phe Phe Arg Asp Lys
                110             115             120 gaa ctg tac gca gca gga gaa atg gat aag gtt gag aaa gtc gaa ctg       651
Glu Leu Tyr Ala Ala Gly Glu Met Asp Lys Val Glu Lys Val Glu Leu
            125             130             135 tcc att tta ggc gaa aaa tac gag atg aat ggt gag ccg gaa aag gag       699
Ser Ile Leu Gly Glu Lys Tyr Glu Met Asn Gly Glu Pro Glu Lys Glu
        140             145             150 cgt ttt aca tat aca tta agc gat ctt cct aca ggc gag cat gaa tat       747
Arg Phe Thr Tyr Thr Leu Ser Asp Leu Pro Thr Gly Glu His Glu Tyr
    155             160             165 act tat ttg gtg aca gtg gat gga cag aca gag gaa gtt acc gat cca       795
Thr Tyr Leu Val Thr Val Asp Gly Gln Thr Glu Glu Val Thr Asp Pro
170             175             180             185 tat aac acg gtg gat gga agg tct gtt gtg gag tat gtg aca tcc gat       843
Tyr Asn Thr Val Asp Gly Arg Ser Val Val Glu Tyr Val Thr Ser Asp
            190             195             200 gtg caa gta tcg gct tca ttt ata ccc gca aag gtt gat tat aac cag       891
Val Gln Val Ser Ala Ser Phe Ile Pro Ala Lys Val Asp Tyr Asn Gln
        205             210             215 aac gct gtg gtg aag gta gac atc gaa tca gaa acg gag aca aaa atc       939
Asn Ala Val Val Lys Val Asp Ile Glu Ser Glu Thr Glu Thr Lys Ile
    220             225             230 cgt gag atg tct atc aat ctt tca gaa atc ggc ggc aaa gag aaa gca       987
Arg Glu Met Ser Ile Asn Leu Ser Glu Ile Gly Gly Lys Glu Lys Ala
235             240             245
```

```
                                                           -continued acc att gat cct gcg ctg aat gaa ttg aca gtt gcg gtc aag caa ggt    1035
Thr Ile Asp Pro Ala Leu Asn Glu Leu Thr Val Ala Val Lys Gln Gly
250                 255                 260                 265 gtg acg gca ggt gtg aaa aac ttg cct atc act gcg att gat gaa ttc    1083
Val Thr Ala Gly Val Lys Asn Leu Pro Ile Thr Ala Ile Asp Glu Phe
                270                 275                 280 gga aat cgc cat gag gga tct gct acc tta gaa gtt cag gcg cgt act    1131
Gly Asn Arg His Glu Gly Ser Ala Thr Leu Glu Val Gln Ala Arg Thr
            285                 290                 295 att aca ggt gaa aaa gca gat ttc gac tgg gat cag tct gtg gtt tat    1179
Ile Thr Gly Glu Lys Ala Asp Phe Asp Trp Asp Gln Ser Val Val Tyr
        300                 305                 310 ttt atg ctg aca gat cga ttc ttt gat ggg gat tca tcg aac aat gac    1227
Phe Met Leu Thr Asp Arg Phe Phe Asp Gly Asp Ser Ser Asn Asn Asp
    315                 320                 325 cct cat ggt att ggc tat gac aca agc aag tct ggt aca tac caa ggc    1275
Pro His Gly Ile Gly Tyr Asp Thr Ser Lys Ser Gly Thr Tyr Gln Gly
330                 335                 340                 345 gga gat ttt aag ggg atc acg caa agg ctt gat tac ttg gac gag ctt    1323
Gly Asp Phe Lys Gly Ile Thr Gln Arg Leu Asp Tyr Leu Asp Glu Leu
                350                 355                 360 gga atc aat acg atc tgg atc agt ccg gtt gtc gat aat atc aaa ttt    1371
Gly Ile Asn Thr Ile Trp Ile Ser Pro Val Val Asp Asn Ile Lys Phe
            365                 370                 375 gat gtt cga cac agt gaa gga cct gat aca cca tat tat gct tac cac    1419
Asp Val Arg His Ser Glu Gly Pro Asp Thr Pro Tyr Tyr Ala Tyr His
        380                 385                 390 ggc tat tgg gcg gat aat ttc ggg gaa ttg aac ccg cat ttc ggt tcc    1467
Gly Tyr Trp Ala Asp Asn Phe Gly Glu Leu Asn Pro His Phe Gly Ser
    395                 400                 405 atg gcg gat ttc cat gaa atg att gat gcg gca cat gaa cgc ggc att    1515
Met Ala Asp Phe His Glu Met Ile Asp Ala Ala His Glu Arg Gly Ile
410                 415                 420                 425 aaa atc atg gtt gat gtg gtg ttg aat cac act ggt tat gga ttg aaa    1563
Lys Ile Met Val Asp Val Val Leu Asn His Thr Gly Tyr Gly Leu Lys
                430                 435                 440 cca ggt gac agc agc agt gtg gcg aac ttc ccg aca gat gag gac cga    1611
Pro Gly Asp Ser Ser Ser Val Ala Asn Phe Pro Thr Asp Glu Asp Arg
            445                 450                 455 gct cgc ttt gac gga atg ctt cgt gat ggc gga tct ggt gaa gtt cga    1659
Ala Arg Phe Asp Gly Met Leu Arg Asp Gly Gly Ser Gly Glu Val Arg
        460                 465                 470 ggc gag ctt gct ggc ctt cca gat ttt ctg acg gaa aac ccg gat gtc    1707
Gly Glu Leu Ala Gly Leu Pro Asp Phe Leu Thr Glu Asn Pro Asp Val
    475                 480                 485 cgt gaa cag gtg gtg caa tgg cag acg gac tgg atc gaa aag tcc agg    1755
Arg Glu Gln Val Val Gln Trp Gln Thr Asp Trp Ile Glu Lys Ser Arg
490                 495                 500                 505 acg gca aag ggc aac acc atc gat tat ttc cgt gtc gac acc gtc aag    1803
Thr Ala Lys Gly Asn Thr Ile Asp Tyr Phe Arg Val Asp Thr Val Lys
                510                 515                 520 cat gtg gaa gac acc act tgg atg gcg ttt aaa aat gct ttg aca aaa    1851
His Val Glu Asp Thr Thr Trp Met Ala Phe Lys Asn Ala Leu Thr Lys
            525                 530                 535 gcg atg ccg gaa cac aag ctg att ggg gaa gca tgg gga gca aat gtc    1899
Ala Met Pro Glu His Lys Leu Ile Gly Glu Ala Trp Gly Ala Asn Val
        540                 545                 550 aat gac gac cta ggt tat ctg aac agc gga atg atg gat tct tta ctg    1947
Asn Asp Asp Leu Gly Tyr Leu Asn Ser Gly Met Met Asp Ser Leu Leu
    555                 560                 565
```

```
gat ttt gat ttc aaa aat tat gcc cgt gac ttt gca aac gga cag ctg      1995
Asp Phe Asp Phe Lys Asn Tyr Ala Arg Asp Phe Ala Asn Gly Gln Leu
570             575                 580                 585 gat gcg gtt cag caa aaa ctt gag gcg cgt aac agc aag ttg aac aat      2043
Asp Ala Val Gln Gln Lys Leu Glu Ala Arg Asn Ser Lys Leu Asn Asn
            590                 595                 600 act gca aca ctt ggt caa ttt tta gga agc cat gac gaa gac cgc ttc      2091
Thr Ala Thr Leu Gly Gln Phe Leu Gly Ser His Asp Glu Asp Arg Phe
                605                 610                 615 tat gag gtg gtg gaa gga gac ctt ggc aag tat caa gtt gct gca tcc      2139
Tyr Glu Val Val Glu Gly Asp Leu Gly Lys Tyr Gln Val Ala Ala Ser
            620                 625                 630 ctt caa ctg acg gca aag ggt cag cct gtt atc tat tac gga gaa gag      2187
Leu Gln Leu Thr Ala Lys Gly Gln Pro Val Ile Tyr Tyr Gly Glu Glu
    635                 640                 645 ctg ggc ttg cct ggt aag aac gat tat ccg tat tat acg aac cgc cag      2235
Leu Gly Leu Pro Gly Lys Asn Asp Tyr Pro Tyr Tyr Thr Asn Arg Gln
650                 655                 660                 665 aac atg cct tgg gat gat gtg gat ggt aat gaa att cta gag cat tat      2283
Asn Met Pro Trp Asp Asp Val Asp Gly Asn Glu Ile Leu Glu His Tyr
                670                 675                 680 caa aaa tta ctg gca ttc cgt aat gat aat ccg aac aca ttt gct aaa      2331
Gln Lys Leu Leu Ala Phe Arg Asn Asp Asn Pro Asn Thr Phe Ala Lys
                685                 690                 695 gga gac cgc aaa aag gta gcg gga tct gac agt gaa gga tat ctt tta      2379
Gly Asp Arg Lys Lys Val Ala Gly Ser Asp Ser Glu Gly Tyr Leu Leu
        700                 705                 710 ttt tca cgg acg tac ggg gaa aat tcc gtt tat gta ggt ttg aat acg      2427
Phe Ser Arg Thr Tyr Gly Glu Asn Ser Val Tyr Val Gly Leu Asn Thr
        715                 720                 725 gaa gct gct gcg aaa gac gta acc ttg aac ttc ggt tct tca gaa gca      2475
Glu Ala Ala Ala Lys Asp Val Thr Leu Asn Phe Gly Ser Ser Glu Ala
730                 735                 740                 745 gtg gtg acg gac cgc tat tcc ggt cag gag tac caa gca aat gaa gaa      2523
Val Val Thr Asp Arg Tyr Ser Gly Gln Glu Tyr Gln Ala Asn Glu Glu
                750                 755                 760 ggc caa gtg acg ttc tct att ccg gcg atg gaa gac ggg gga acg gtc      2571
Gly Gln Val Thr Phe Ser Ile Pro Ala Met Glu Asp Gly Gly Thr Val
            765                 770                 775 ctg ctt gaa gtg gaa aat gga gca gtg cca cct gtg gag gaa gaa cca      2619
Leu Leu Glu Val Glu Asn Gly Ala Val Pro Pro Val Glu Glu Glu Pro
                780                 785                 790 act gag cca ggt gaa atc gaa gaa aac acg ctt cgg att cac tac cag      2667
Thr Glu Pro Gly Glu Ile Glu Glu Asn Thr Leu Arg Ile His Tyr Gln
795                 800                 805 cgc aca gac aac agc tac gaa aac ctt ggt cta tgg tta tgg gga gac      2715
Arg Thr Asp Asn Ser Tyr Glu Asn Leu Gly Leu Trp Leu Trp Gly Asp
810                 815                 820                 825 gtc gcg gca cca tct gaa aac tgg cca tca ggc ggc aca ccg ttc caa      2763
Val Ala Ala Pro Ser Glu Asn Trp Pro Ser Gly Gly Thr Pro Phe Gln
                830                 835                 840 gca ggt aat gta aca gac tat ggt gca tat gtc gat gtg gaa ttg gca      2811
Ala Gly Asn Val Thr Asp Tyr Gly Ala Tyr Val Asp Val Glu Leu Ala
                845                 850                 855 gaa gat gct caa aat att gga ttc ctt gtt ttg aac acc aca aac ggt      2859
Glu Asp Ala Gln Asn Ile Gly Phe Leu Val Leu Asn Thr Thr Asn Gly
            860                 865                 870 gac aag gac ggc ggc gac aaa gca gta gaa ttg ttc agt ccg gat tta      2907
Asp Lys Asp Gly Gly Asp Lys Ala Val Glu Leu Phe Ser Pro Asp Leu
```

```
                875             880             885
aat gag att tgg atc aaa caa ggc tct gat gaa gta ttt tta tat gaa    2955
Asn Glu Ile Trp Ile Lys Gln Gly Ser Asp Glu Val Phe Leu Tyr Glu
890             895             900             905 ccg gtg gac ctt ccg gca aat acg gtc cgc att cat tat gaa aga acc    3003
Pro Val Asp Leu Pro Ala Asn Thr Val Arg Ile His Tyr Glu Arg Thr
            910             915             920 aat gcc gac tat gaa ggc tgg ggg tta tgg aac tgg gag gat gtc gag    3051
Asn Ala Asp Tyr Glu Gly Trp Gly Leu Trp Asn Trp Glu Asp Val Glu
        925             930             935 tcc cca tct gac ggg tgg ccg aac ggt gcc gca gat gct gca ggt atc    3099
Ser Pro Ser Asp Gly Trp Pro Asn Gly Ala Ala Asp Ala Ala Gly Ile
            940             945             950 ggt aaa tac ggt gct tac tac gac atc aag ctg aaa gaa gat gct aat    3147
Gly Lys Tyr Gly Ala Tyr Tyr Asp Ile Lys Leu Lys Glu Asp Ala Asn
    955             960             965 aaa att ggt ttc ctt ttt gtg aac aaa caa tct ggt ggc caa acg gga    3195
Lys Ile Gly Phe Leu Phe Val Asn Lys Gln Ser Gly Gly Gln Thr Gly
970             975             980             985 gat atg acg ttt gat atg ctg aaa caa tac aac caa ctt ttt gta aaa   3243
Asp Met Thr Phe Asp Met Leu Lys Gln Tyr Asn Gln Leu Phe Val Lys
            990             995             1000 gag ggc gag gac  aag gtc tac acc aat  cct tac ggg acc gtg  cca    3288
Glu Gly Glu Asp  Lys Val Tyr Thr Asn  Pro Tyr Gly Thr Val  Pro
        1005            1010            1015 ttg gcg ctt gtg  tct gga gag gta ttg  tca gac aag ttg atc  agt    3333
Leu Ala Leu Val  Ser Gly Glu Val Leu  Ser Asp Lys Leu Ile  Ser
        1020            1025            1030 ctt act ttt acc  agg aca gaa gga ttg  gat ttg gag gaa ttg  aaa    3378
Leu Thr Phe Thr  Arg Thr Glu Gly Leu  Asp Leu Glu Glu Leu  Lys
        1035            1040            1045 gaa cag cta gaa  atc aag gat gtg gac  ggg aac gat gtt tcg  ttt    3423
Glu Gln Leu Glu  Ile Lys Asp Val Asp  Gly Asn Asp Val Ser  Phe
        1050            1055            1060 aca gat gtg aca  att gaa ggc gag aaa  acg gtc cat gtc cac  ggc    3468
Thr Asp Val Thr  Ile Glu Gly Glu Lys  Thr Val His Val His  Gly
        1065            1070            1075 gag ttt gac ttg  gag aaa atc ccg ttc  tct gtg acc tat ctg  gac    3513
Glu Phe Asp Leu  Glu Lys Ile Pro Phe  Ser Val Thr Tyr Leu  Asp
        1080            1085            1090 cgc acc att tct  gta aaa tca ggc tgg  aaa ctg atc gac gaa  atg    3558
Arg Thr Ile Ser  Val Lys Ser Gly Trp  Lys Leu Ile Asp Glu  Met
        1095            1100            1105 tat gcc tat gat  gga aag ctt ggg gca  gaa ttg cat gaa gac  ggg    3603
Tyr Ala Tyr Asp  Gly Lys Leu Gly Ala  Glu Leu His Glu Asp  Gly
        1110            1115            1120 acg gct act ttg  aaa gta tgg tcg cca  aaa gcg gac aat gtg  tct    3648
Thr Ala Thr Leu  Lys Val Trp Ser Pro  Lys Ala Asp Asn Val  Ser
        1125            1130            1135 gtt gta ctt tat  gac aaa gtt gac cag  aac gag gtt gta gac  acc    3693
Val Val Leu Tyr  Asp Lys Val Asp Gln  Asn Glu Val Val Asp  Thr
        1140            1145            1150 att gaa atg gta  aaa ggg gac cgc ggt  gtc tgg tct gta aag  cta    3738
Ile Glu Met Val  Lys Gly Asp Arg Gly  Val Trp Ser Val Lys  Leu
        1155            1160            1165 act aag gat aat  aca ggc ctt gat agt  ttg aaa ggt tac tat  tac    3783
Thr Lys Asp Asn  Thr Gly Leu Asp Ser  Leu Lys Gly Tyr Tyr  Tyr
        1170            1175            1180 cac tat gaa atc  acg cat ggt gac gta  acg aat ctt gct cta  gat    3828
```

```
                                                            -continued

His Tyr Glu Ile Thr His Gly Asp Val Thr Asn Leu Ala Leu Asp
            1185                1190                1195 ccg tat gcc aaa tca atg gcg gcg tgg aat aac gaa gcg ggg gac         3873
Pro Tyr Ala Lys Ser Met Ala Ala Trp Asn Asn Glu Ala Gly Asp
            1200                1205                1210 aag gta gga aaa gcg gcg atc gtg gac atc ggc tcc att ggg cct         3918
Lys Val Gly Lys Ala Ala Ile Val Asp Ile Gly Ser Ile Gly Pro
            1215                1220                1225 gag ctt gat tat gcc gac atc cct ggc ttt gaa aag cgc gaa gac         3963
Glu Leu Asp Tyr Ala Asp Ile Pro Gly Phe Glu Lys Arg Glu Asp
            1230                1235                1240 acc atc atc tac gag gtg cat gta cgt gac ttc act tcc gac ccg         4008
Thr Ile Ile Tyr Glu Val His Val Arg Asp Phe Thr Ser Asp Pro
            1245                1250                1255 aat atc ggt gag gac ctg aag gca cag ttc ggt aca ttt gct tct         4053
Asn Ile Gly Glu Asp Leu Lys Ala Gln Phe Gly Thr Phe Ala Ser
            1260                1265                1270 ttc gtg gaa aag ctg gat tac att caa gag tta ggt gtc act cac         4098
Phe Val Glu Lys Leu Asp Tyr Ile Gln Glu Leu Gly Val Thr His
            1275                1280                1285 att caa ttg ttg cct gtg atg agc tat tat ttc agc aat gaa ttt         4143
Ile Gln Leu Leu Pro Val Met Ser Tyr Tyr Phe Ser Asn Glu Phe
            1290                1295                1300 gag tct ggg gag cgc atg ctg gag tat gct tca acg ggg acg aat         4188
Glu Ser Gly Glu Arg Met Leu Glu Tyr Ala Ser Thr Gly Thr Asn
            1305                1310                1315 tac aat tgg ggc tat gac ccg cac aat tac ttc tcc tta tcc ggc         4233
Tyr Asn Trp Gly Tyr Asp Pro His Asn Tyr Phe Ser Leu Ser Gly
            1320                1325                1330 atg tac tcc gaa aac cct gag gac ccg gaa ctg aga atc aaa gaa         4278
Met Tyr Ser Glu Asn Pro Glu Asp Pro Glu Leu Arg Ile Lys Glu
            1335                1340                1345 ttc aag aat ctg atc aac gag att cat aag cgc gac atg ggt gtg         4323
Phe Lys Asn Leu Ile Asn Glu Ile His Lys Arg Asp Met Gly Val
            1350                1355                1360 gta ctt gat gtg gtg ttt aac cac acc gca cag gtt cac att ttc         4368
Val Leu Asp Val Val Phe Asn His Thr Ala Gln Val His Ile Phe
            1365                1370                1375 gag gac ctt gta cca aac tac tat cac ttc atg gat gcg gac gga         4413
Glu Asp Leu Val Pro Asn Tyr Tyr His Phe Met Asp Ala Asp Gly
            1380                1385                1390 acc cca aga act agc ttt ggc ggt gga cgt ctt gga acg aca cat         4458
Thr Pro Arg Thr Ser Phe Gly Gly Gly Arg Leu Gly Thr Thr His
            1395                1400                1405 gaa atg tcc cgc cgt gtg ctc gta gat tcc atc aag cat tgg gtg         4503
Glu Met Ser Arg Arg Val Leu Val Asp Ser Ile Lys His Trp Val
            1410                1415                1420 gat gaa tat aag gtg gac gga ttc cgt ttt gac atg atg ggt gac         4548
Asp Glu Tyr Lys Val Asp Gly Phe Arg Phe Asp Met Met Gly Asp
            1425                1430                1435 cat gat gca gag agt att cag att gct ttt gac gaa gcc aaa aaa         4593
His Asp Ala Glu Ser Ile Gln Ile Ala Phe Asp Glu Ala Lys Lys
            1440                1445                1450 ttg aac ccg aat atc gtc atg atc ggg gaa ggc tgg gta aca ttt         4638
Leu Asn Pro Asn Ile Val Met Ile Gly Glu Gly Trp Val Thr Phe
            1455                1460                1465 gct ggt gac gag ggc gag ccg gtc cag gcg gcc gat caa caa tgg         4683
Ala Gly Asp Glu Gly Glu Pro Val Gln Ala Ala Asp Gln Gln Trp
            1470                1475                1480
```

```
atg caa tat acc gaa gca gtg ggt agc ttc tcg gat gaa ttc cgc      4728
Met Gln Tyr Thr Glu Ala Val Gly Ser Phe Ser Asp Glu Phe Arg
        1485            1490            1495 aac gag ctg aaa tcc ggt ttc gga agc gaa gga cag cca cgt ttc      4773
Asn Glu Leu Lys Ser Gly Phe Gly Ser Glu Gly Gln Pro Arg Phe
        1500            1505            1510 atc aca ggt ggc gcg gtc aat gtg caa caa att ttc gat aac atc      4818
Ile Thr Gly Gly Ala Val Asn Val Gln Gln Ile Phe Asp Asn Ile
        1515            1520            1525 aaa gca cag cct cat aac ttt atg gcc gat caa cca ggc gat gtg      4863
Lys Ala Gln Pro His Asn Phe Met Ala Asp Gln Pro Gly Asp Val
        1530            1535            1540 gtc caa tac atc gag gcc cat gac aac ctg acg tta tac gat gtc      4908
Val Gln Tyr Ile Glu Ala His Asp Asn Leu Thr Leu Tyr Asp Val
        1545            1550            1555 atc gca caa tct atc aaa aaa gat ccg gaa atc gcg gaa aac gat      4953
Ile Ala Gln Ser Ile Lys Lys Asp Pro Glu Ile Ala Glu Asn Asp
        1560            1565            1570 tta gag att cat aag cgt att cgc gtg ggt aat gcc atg gtc ttg      4998
Leu Glu Ile His Lys Arg Ile Arg Val Gly Asn Ala Met Val Leu
        1575            1580            1585 acg tct caa ggt acg gca ttc tta cac gca gga cag gaa ttt ggt      5043
Thr Ser Gln Gly Thr Ala Phe Leu His Ala Gly Gln Glu Phe Gly
        1590            1595            1600 cgt aca aag caa tgg aga gca cct gca acg gag gca ccg tac aag      5088
Arg Thr Lys Gln Trp Arg Ala Pro Ala Thr Glu Ala Pro Tyr Lys
        1605            1610            1615 tct acg tat atg aca gat gct gat ggc aat ccg ttc gtg tat cca      5133
Ser Thr Tyr Met Thr Asp Ala Asp Gly Asn Pro Phe Val Tyr Pro
        1620            1625            1630 tat ttc atc cac gat tcc tat gat tcc tcg gat atc atc aat cgt      5178
Tyr Phe Ile His Asp Ser Tyr Asp Ser Ser Asp Ile Ile Asn Arg
        1635            1640            1645 ttt gat tgg gaa aaa gcg aca gat gcc gag aaa tac cct gtc aac      5223
Phe Asp Trp Glu Lys Ala Thr Asp Ala Glu Lys Tyr Pro Val Asn
        1650            1655            1660 aat gtg aca cgt gac tac acg gca ggc ttg atc gag ctg cgt cgt      5268
Asn Val Thr Arg Asp Tyr Thr Ala Gly Leu Ile Glu Leu Arg Arg
        1665            1670            1675 tca tct gat gct ttc cgt tta ggt tct cgt gaa ttg gtc gat tcc      5313
Ser Ser Asp Ala Phe Arg Leu Gly Ser Arg Glu Leu Val Asp Ser
        1680            1685            1690 aat gtg aca atg gtt gat gcc ccg gaa atc aag gag cag gat ctc      5358
Asn Val Thr Met Val Asp Ala Pro Glu Ile Lys Glu Gln Asp Leu
        1695            1700            1705 gtt gtt gcc tac cgc agt gtt tcg act gcc ggt gtg gag tat tac      5403
Val Val Ala Tyr Arg Ser Val Ser Thr Ala Gly Val Glu Tyr Tyr
        1710            1715            1720 aca ttc gtg aat gcg gac act tcc agt aga aca ttg acc tta ggg      5448
Thr Phe Val Asn Ala Asp Thr Ser Ser Arg Thr Leu Thr Leu Gly
        1725            1730            1735 cag gat ttg aca gag ggc gta gtg gtg gtc gat gca gaa gag gct      5493
Gln Asp Leu Thr Glu Gly Val Val Val Val Asp Ala Glu Glu Ala
        1740            1745            1750 aat gta gcc ggt gta gct gag cct gca ggt ttc gaa ttg acg gca      5538
Asn Val Ala Gly Val Ala Glu Pro Ala Gly Phe Glu Leu Thr Ala
        1755            1760            1765 gaa ggc atc aca ctt gag cca ttg act acg gtt gtc gtc cgt gta      5583
Glu Gly Ile Thr Leu Glu Pro Leu Thr Thr Val Val Val Arg Val
        1770            1775            1780
```

```
ggc gag cag gaa ggg aca gac ccg ggt gat ggg gac ggc gat ggc      5628
Gly Glu Gln Glu Gly Thr Asp Pro Gly Asp Gly Asp Gly Asp Gly
        1785                1790                1795 aat acg ccg cca cca ggc gac ggc gat ggc gat gga aac acg cca      5673
Asn Thr Pro Pro Pro Gly Asp Gly Asp Gly Asp Gly Asn Thr Pro
        1800                1805                1810 cca cca ggg gat ggg gat ggc gat gga aac acg cct cct cca ggc      5718
Pro Pro Gly Asp Gly Asp Gly Asp Gly Asn Thr Pro Pro Pro Gly
        1815                1820                1825 aac ggt aat ggc aat aat cca gga aca cca cca gga aag ggt gga      5763
Asn Gly Asn Gly Asn Asn Pro Gly Thr Pro Pro Gly Lys Gly Gly
        1830                1835                1840 gaa aac cct ggt aaa ggc aaa aac gac aaa aca ccg cct ggc aaa      5808
Glu Asn Pro Gly Lys Gly Lys Asn Asp Lys Thr Pro Pro Gly Lys
        1845                1850                1855 ggt ggg gac aat cca ggt aag ggg aac aag cta cca ctt acc gca      5853
Gly Gly Asp Asn Pro Gly Lys Gly Asn Lys Leu Pro Leu Thr Ala
        1860                1865                1870 acc gga aca ctt aat tac atc ctg ttt ggt gca ata atg ttg gtt      5898
Thr Gly Thr Leu Asn Tyr Ile Leu Phe Gly Ala Ile Met Leu Val
        1875                1880                1885 ctt ggg acg ctg ctg tat cta ggg gtc aga aga aaa gca gga ttg      5943
Leu Gly Thr Leu Leu Tyr Leu Gly Val Arg Arg Lys Ala Gly Leu
        1890                1895                1900 aaa gaa aaa acc tta taaaaacaac ggaaaagtgt ggcaggggaa atcccgcca   5998
Lys Glu Lys Thr Leu
            1905 cacttttcg ttattataag gcattatttg cttgtagatt aaggattcgc tataggttat 6058 tttgtgtaac gtacattact tttccgttgg gccatattta ttttccatac cgctcatttt 6118 tcttttccat tgggaccaca ttta                                       6142

<210> SEQ ID NO 2
<211> LENGTH: 1938
<212> TYPE: PRT
<213> ORGANISM: Bacillus sp.

<400> SEQUENCE: 2

Met Lys Lys Arg Phe Gln Arg Gly Met Ala Gly Leu Leu Ser Ile Leu
        -30                 -25                 -20

Leu Ile Val Ser Met Phe Ala Gly Tyr Leu Pro Ala Arg Ala Ala Ala
        -15                 -10                 -5              -1

Glu Thr Gly Asp Lys Arg Ile Glu Phe Ser Tyr Glu Arg Pro Asp Gly
1               5                   10                  15

Asn Tyr Glu Gly Trp Asn Leu Trp Val Trp Gly Thr Gly Val Lys Asp
                20                  25                  30

Asp Gln Ile Asp Phe Thr Glu Phe Lys Glu Gly Lys Ala Tyr Ala Asp
        35                  40                  45

Ile Ala Val Ser Asp Asn Ala Asp Lys Val Gly Phe Ile Ile Arg Lys
        50                  55                  60

Gly Asp Trp Glu Glu Lys Asp Phe Asp Gly Asp Arg Ser Ile Thr Ile
65                  70                  75                  80

Asn Lys Ile Asp Asn Ile Thr Lys Val His Val Thr Ser Gln Gln Glu
                85                  90                  95

Lys Phe Gly Gln Ile Pro Asp Gly Ser Pro Val Val Ala Asp Gly
            100                 105                 110

Asn Ala Asp Phe Phe Phe Arg Asp Lys Glu Leu Tyr Ala Ala Gly Glu
```

-continued

```
            115                 120                 125
Met Asp Lys Val Glu Lys Val Glu Leu Ser Ile Leu Gly Glu Lys Tyr
    130                 135                 140
Glu Met Asn Gly Glu Pro Glu Lys Glu Arg Phe Thr Tyr Thr Leu Ser
145                 150                 155                 160
Asp Leu Pro Thr Gly Glu His Glu Tyr Thr Tyr Leu Val Thr Val Asp
                165                 170                 175
Gly Gln Thr Glu Glu Val Thr Asp Pro Tyr Asn Thr Val Asp Gly Arg
            180                 185                 190
Ser Val Val Glu Tyr Val Thr Ser Asp Val Gln Val Ser Ala Ser Phe
            195                 200                 205
Ile Pro Ala Lys Val Asp Tyr Asn Gln Asn Ala Val Val Lys Val Asp
    210                 215                 220
Ile Glu Ser Glu Thr Glu Thr Lys Ile Arg Glu Met Ser Ile Asn Leu
225                 230                 235                 240
Ser Glu Ile Gly Gly Lys Glu Lys Ala Thr Ile Asp Pro Ala Leu Asn
                245                 250                 255
Glu Leu Thr Val Ala Val Lys Gln Gly Val Thr Ala Gly Val Lys Asn
            260                 265                 270
Leu Pro Ile Thr Ala Ile Asp Glu Phe Gly Asn Arg His Glu Gly Ser
    275                 280                 285
Ala Thr Leu Glu Val Gln Ala Arg Thr Ile Thr Gly Glu Lys Ala Asp
    290                 295                 300
Phe Asp Trp Asp Gln Ser Val Val Tyr Phe Met Leu Thr Asp Arg Phe
305                 310                 315                 320
Phe Asp Gly Asp Ser Ser Asn Asn Asp Pro His Gly Ile Gly Tyr Asp
                325                 330                 335
Thr Ser Lys Ser Gly Thr Tyr Gln Gly Gly Asp Phe Lys Gly Ile Thr
                340                 345                 350
Gln Arg Leu Asp Tyr Leu Asp Glu Leu Gly Ile Asn Thr Ile Trp Ile
            355                 360                 365
Ser Pro Val Val Asp Asn Ile Lys Phe Asp Val Arg His Ser Glu Gly
    370                 375                 380
Pro Asp Thr Pro Tyr Tyr Ala Tyr His Gly Tyr Trp Ala Asp Asn Phe
385                 390                 395                 400
Gly Glu Leu Asn Pro His Phe Gly Ser Met Ala Asp Phe His Glu Met
                405                 410                 415
Ile Asp Ala Ala His Glu Arg Gly Ile Lys Ile Met Val Asp Val Val
            420                 425                 430
Leu Asn His Thr Gly Tyr Gly Leu Lys Pro Gly Asp Ser Ser Ser Val
            435                 440                 445
Ala Asn Phe Pro Thr Asp Glu Asp Arg Ala Arg Phe Asp Gly Met Leu
    450                 455                 460
Arg Asp Gly Gly Ser Gly Glu Val Arg Gly Glu Leu Ala Gly Leu Pro
465                 470                 475                 480
Asp Phe Leu Thr Glu Asn Pro Asp Val Arg Glu Gln Val Val Gln Trp
                485                 490                 495
Gln Thr Asp Trp Ile Glu Lys Ser Arg Thr Ala Lys Gly Asn Thr Ile
            500                 505                 510
Asp Tyr Phe Arg Val Asp Thr Val Lys His Val Glu Asp Thr Thr Trp
            515                 520                 525
Met Ala Phe Lys Asn Ala Leu Thr Lys Ala Met Pro Glu His Lys Leu
    530                 535                 540
```

```
Ile Gly Glu Ala Trp Gly Ala Asn Val Asn Asp Asp Leu Gly Tyr Leu
545                 550                 555                 560

Asn Ser Gly Met Met Asp Ser Leu Leu Asp Phe Asp Phe Lys Asn Tyr
                565                 570                 575

Ala Arg Asp Phe Ala Asn Gly Gln Leu Asp Ala Val Gln Gln Lys Leu
            580                 585                 590

Glu Ala Arg Asn Ser Lys Leu Asn Asn Thr Ala Thr Leu Gly Gln Phe
        595                 600                 605

Leu Gly Ser His Asp Glu Asp Arg Phe Tyr Glu Val Val Glu Gly Asp
    610                 615                 620

Leu Gly Lys Tyr Gln Val Ala Ala Ser Leu Gln Leu Thr Ala Lys Gly
625                 630                 635                 640

Gln Pro Val Ile Tyr Tyr Gly Glu Glu Leu Gly Leu Pro Gly Lys Asn
                645                 650                 655

Asp Tyr Pro Tyr Tyr Thr Asn Arg Gln Asn Met Pro Trp Asp Asp Val
            660                 665                 670

Asp Gly Asn Glu Ile Leu Glu His Tyr Gln Lys Leu Leu Ala Phe Arg
        675                 680                 685

Asn Asp Asn Pro Asn Thr Phe Ala Lys Gly Asp Arg Lys Lys Val Ala
    690                 695                 700

Gly Ser Asp Ser Glu Gly Tyr Leu Leu Phe Ser Arg Thr Tyr Gly Glu
705                 710                 715                 720

Asn Ser Val Tyr Val Gly Leu Asn Thr Glu Ala Ala Lys Asp Val
                725                 730                 735

Thr Leu Asn Phe Gly Ser Ser Glu Ala Val Thr Asp Arg Tyr Ser
            740                 745                 750

Gly Gln Glu Tyr Gln Ala Asn Glu Glu Gly Gln Val Thr Phe Ser Ile
        755                 760                 765

Pro Ala Met Glu Asp Gly Gly Thr Val Leu Leu Glu Val Glu Asn Gly
    770                 775                 780

Ala Val Pro Pro Val Glu Glu Pro Thr Glu Pro Gly Glu Ile Glu
785                 790                 795                 800

Glu Asn Thr Leu Arg Ile His Tyr Gln Arg Thr Asp Asn Ser Tyr Glu
                805                 810                 815

Asn Leu Gly Leu Trp Leu Trp Gly Asp Val Ala Ala Pro Ser Glu Asn
            820                 825                 830

Trp Pro Ser Gly Gly Thr Pro Phe Gln Ala Gly Asn Val Thr Asp Tyr
        835                 840                 845

Gly Ala Tyr Val Asp Val Glu Leu Ala Glu Asp Ala Gln Asn Ile Gly
    850                 855                 860

Phe Leu Val Leu Asn Thr Thr Asn Gly Asp Lys Asp Gly Gly Asp Lys
865                 870                 875                 880

Ala Val Glu Leu Phe Ser Pro Asp Leu Asn Glu Ile Trp Ile Lys Gln
                885                 890                 895

Gly Ser Asp Glu Val Phe Leu Tyr Glu Pro Val Asp Leu Pro Ala Asn
            900                 905                 910

Thr Val Arg Ile His Tyr Glu Arg Thr Asn Ala Asp Tyr Glu Gly Trp
        915                 920                 925

Gly Leu Trp Asn Trp Glu Asp Val Glu Ser Pro Ser Asp Gly Trp Pro
    930                 935                 940

Asn Gly Ala Ala Asp Ala Ala Gly Ile Gly Lys Tyr Gly Ala Tyr Tyr
945                 950                 955                 960
```

-continued

```
Asp Ile Lys Leu Lys Glu Asp Ala Asn Lys Ile Gly Phe Leu Phe Val
                965                 970                 975
Asn Lys Gln Ser Gly Gly Gln Thr Gly Asp Met Thr Phe Asp Met Leu
            980                 985                 990
Lys Gln Tyr Asn Gln Leu Phe Val Lys Glu Gly Glu Asp Lys Val Tyr
        995                 1000                1005
Thr Asn Pro Tyr Gly Thr Val Pro Leu Ala Leu Val Ser Gly Glu
    1010                1015                1020
Val Leu Ser Asp Lys Leu Ile Ser Leu Thr Phe Thr Arg Thr Glu
    1025                1030                1035
Gly Leu Asp Leu Glu Glu Leu Lys Glu Gln Leu Glu Ile Lys Asp
    1040                1045                1050
Val Asp Gly Asn Asp Val Ser Phe Thr Asp Val Thr Ile Glu Gly
    1055                1060                1065
Glu Lys Thr Val His Val His Gly Glu Phe Asp Leu Glu Lys Ile
    1070                1075                1080
Pro Phe Ser Val Thr Tyr Leu Asp Arg Thr Ile Ser Val Lys Ser
    1085                1090                1095
Gly Trp Lys Leu Ile Asp Glu Met Tyr Ala Tyr Asp Gly Lys Leu
    1100                1105                1110
Gly Ala Glu Leu His Glu Asp Gly Thr Ala Thr Leu Lys Val Trp
    1115                1120                1125
Ser Pro Lys Ala Asp Asn Val Ser Val Val Leu Tyr Asp Lys Val
    1130                1135                1140
Asp Gln Asn Glu Val Val Asp Thr Ile Glu Met Val Lys Gly Asp
    1145                1150                1155
Arg Gly Val Trp Ser Val Lys Leu Thr Lys Asp Asn Thr Gly Leu
    1160                1165                1170
Asp Ser Leu Lys Gly Tyr Tyr Tyr His Tyr Glu Ile Thr His Gly
    1175                1180                1185
Asp Val Thr Asn Leu Ala Leu Asp Pro Tyr Ala Lys Ser Met Ala
    1190                1195                1200
Ala Trp Asn Asn Glu Ala Gly Asp Lys Val Gly Lys Ala Ala Ile
    1205                1210                1215
Val Asp Ile Gly Ser Ile Gly Pro Glu Leu Asp Tyr Ala Asp Ile
    1220                1225                1230
Pro Gly Phe Glu Lys Arg Glu Asp Thr Ile Ile Tyr Glu Val His
    1235                1240                1245
Val Arg Asp Phe Thr Ser Asp Pro Asn Ile Gly Glu Asp Leu Lys
    1250                1255                1260
Ala Gln Phe Gly Thr Phe Ala Ser Phe Val Glu Lys Leu Asp Tyr
    1265                1270                1275
Ile Gln Glu Leu Gly Val Thr His Ile Gln Leu Leu Pro Val Met
    1280                1285                1290
Ser Tyr Tyr Phe Ser Asn Glu Phe Glu Ser Gly Glu Arg Met Leu
    1295                1300                1305
Glu Tyr Ala Ser Thr Gly Thr Asn Tyr Asn Trp Gly Tyr Asp Pro
    1310                1315                1320
His Asn Tyr Phe Ser Leu Ser Gly Met Tyr Ser Glu Asn Pro Glu
    1325                1330                1335
Asp Pro Glu Leu Arg Ile Lys Glu Phe Lys Asn Leu Ile Asn Glu
    1340                1345                1350
Ile His Lys Arg Asp Met Gly Val Val Leu Asp Val Val Phe Asn
```

-continued

|  |  |  |  |  |  |  |  |  |  |
|---|---|---|---|---|---|---|---|---|---|
|  | 1355 |  |  | 1360 |  |  | 1365 |  |  |
| His | Thr | Ala | Gln | Val | His | Ile | Phe | Glu | Asp | Leu | Val | Pro | Asn | Tyr |
| 1370 |  |  |  | 1375 |  |  |  | 1380 |  |
| Tyr | His | Phe | Met | Asp | Ala | Asp | Gly | Thr | Pro | Arg | Thr | Ser | Phe | Gly |
| 1385 |  |  |  | 1390 |  |  |  | 1395 |  |
| Gly | Gly | Arg | Leu | Gly | Thr | Thr | His | Glu | Met | Ser | Arg | Arg | Val | Leu |
| 1400 |  |  |  | 1405 |  |  |  | 1410 |  |
| Val | Asp | Ser | Ile | Lys | His | Trp | Val | Asp | Glu | Tyr | Lys | Val | Asp | Gly |
| 1415 |  |  |  | 1420 |  |  |  | 1425 |  |
| Phe | Arg | Phe | Asp | Met | Met | Gly | Asp | His | Asp | Ala | Glu | Ser | Ile | Gln |
| 1430 |  |  |  | 1435 |  |  |  | 1440 |  |
| Ile | Ala | Phe | Asp | Glu | Ala | Lys | Lys | Leu | Asn | Pro | Asn | Ile | Val | Met |
| 1445 |  |  |  | 1450 |  |  |  | 1455 |  |
| Ile | Gly | Glu | Gly | Trp | Val | Thr | Phe | Ala | Gly | Asp | Glu | Gly | Glu | Pro |
| 1460 |  |  |  | 1465 |  |  |  | 1470 |  |
| Val | Gln | Ala | Ala | Asp | Gln | Gln | Trp | Met | Gln | Tyr | Thr | Glu | Ala | Val |
| 1475 |  |  |  | 1480 |  |  |  | 1485 |  |
| Gly | Ser | Phe | Ser | Asp | Glu | Phe | Arg | Asn | Glu | Leu | Lys | Ser | Gly | Phe |
| 1490 |  |  |  | 1495 |  |  |  | 1500 |  |
| Gly | Ser | Glu | Gly | Gln | Pro | Arg | Phe | Ile | Thr | Gly | Gly | Ala | Val | Asn |
| 1505 |  |  |  | 1510 |  |  |  | 1515 |  |
| Val | Gln | Gln | Ile | Phe | Asp | Asn | Ile | Lys | Ala | Gln | Pro | His | Asn | Phe |
| 1520 |  |  |  | 1525 |  |  |  | 1530 |  |
| Met | Ala | Asp | Gln | Pro | Gly | Asp | Val | Val | Gln | Tyr | Ile | Glu | Ala | His |
| 1535 |  |  |  | 1540 |  |  |  | 1545 |  |
| Asp | Asn | Leu | Thr | Leu | Tyr | Asp | Val | Ile | Ala | Gln | Ser | Ile | Lys | Lys |
| 1550 |  |  |  | 1555 |  |  |  | 1560 |  |
| Asp | Pro | Glu | Ile | Ala | Glu | Asn | Asp | Leu | Glu | Ile | His | Lys | Arg | Ile |
| 1565 |  |  |  | 1570 |  |  |  | 1575 |  |
| Arg | Val | Gly | Asn | Ala | Met | Val | Leu | Thr | Ser | Gln | Gly | Thr | Ala | Phe |
| 1580 |  |  |  | 1585 |  |  |  | 1590 |  |
| Leu | His | Ala | Gly | Gln | Glu | Phe | Gly | Arg | Thr | Lys | Gln | Trp | Arg | Ala |
| 1595 |  |  |  | 1600 |  |  |  | 1605 |  |
| Pro | Ala | Thr | Glu | Ala | Pro | Tyr | Lys | Ser | Thr | Tyr | Met | Thr | Asp | Ala |
| 1610 |  |  |  | 1615 |  |  |  | 1620 |  |
| Asp | Gly | Asn | Pro | Phe | Val | Tyr | Pro | Tyr | Phe | Ile | His | Asp | Ser | Tyr |
| 1625 |  |  |  | 1630 |  |  |  | 1635 |  |
| Asp | Ser | Ser | Asp | Ile | Ile | Asn | Arg | Phe | Asp | Trp | Glu | Lys | Ala | Thr |
| 1640 |  |  |  | 1645 |  |  |  | 1650 |  |
| Asp | Ala | Glu | Lys | Tyr | Pro | Val | Asn | Asn | Val | Thr | Arg | Asp | Tyr | Thr |
| 1655 |  |  |  | 1660 |  |  |  | 1665 |  |
| Ala | Gly | Leu | Ile | Glu | Leu | Arg | Arg | Ser | Ser | Asp | Ala | Phe | Arg | Leu |
| 1670 |  |  |  | 1675 |  |  |  | 1680 |  |
| Gly | Ser | Arg | Glu | Leu | Val | Asp | Ser | Asn | Val | Thr | Met | Val | Asp | Ala |
| 1685 |  |  |  | 1690 |  |  |  | 1695 |  |
| Pro | Glu | Ile | Lys | Glu | Gln | Asp | Leu | Val | Val | Ala | Tyr | Arg | Ser | Val |
| 1700 |  |  |  | 1705 |  |  |  | 1710 |  |
| Ser | Thr | Ala | Gly | Val | Glu | Tyr | Tyr | Thr | Phe | Val | Asn | Ala | Asp | Thr |
| 1715 |  |  |  | 1720 |  |  |  | 1725 |  |
| Ser | Ser | Arg | Thr | Leu | Thr | Leu | Gly | Gln | Asp | Leu | Thr | Glu | Gly | Val |
| 1730 |  |  |  | 1735 |  |  |  | 1740 |  |
| Val | Val | Val | Asp | Ala | Glu | Glu | Ala | Asn | Val | Ala | Gly | Val | Ala | Glu |
| 1745 |  |  |  | 1750 |  |  |  | 1755 |  |

-continued

```
Pro Ala Gly Phe Glu Leu Thr Ala Glu Gly Ile Thr Leu Glu Pro
    1760                1765                1770

Leu Thr Thr Val Val Val Arg Val Gly Glu Gln Glu Gly Thr Asp
    1775                1780                1785

Pro Gly Asp Gly Asp Gly Asp Gly Asn Thr Pro Pro Pro Gly Asp
    1790                1795                1800

Gly Asp Gly Asp Gly Asn Thr Pro Pro Gly Asp Gly Asp Gly
    1805                1810                1815

Asp Gly Asn Thr Pro Pro Gly Asn Gly Asn Gly Asn Asn Pro
    1820                1825                1830

Gly Thr Pro Pro Gly Lys Gly Gly Glu Asn Pro Gly Lys Gly Lys
    1835                1840                1845

Asn Asp Lys Thr Pro Pro Gly Lys Gly Gly Asp Asn Pro Gly Lys
    1850                1855                1860

Gly Asn Lys Leu Pro Leu Thr Ala Thr Gly Thr Leu Asn Tyr Ile
    1865                1870                1875

Leu Phe Gly Ala Ile Met Leu Val Leu Gly Thr Leu Leu Tyr Leu
    1880                1885                1890

Gly Val Arg Arg Lys Ala Gly Leu Lys Glu Lys Thr Leu
    1895                1900                1905
```

<210> SEQ ID NO 3
<211> LENGTH: 833
<212> TYPE: PRT
<213> ORGANISM: Bacillus sp.

<400> SEQUENCE: 3

```
Met Lys Lys Arg Phe Gln Arg Gly Met Ala Gly Leu Leu Ser Ile Leu
1               5                   10                  15

Leu Ile Val Ser Met Phe Ala Gly Tyr Leu Pro Ala Arg Ala Ala Ala
            20                  25                  30

Glu Thr Gly Asp Lys Arg Ile Glu Phe Ser Tyr Glu Arg Pro Asp Gly
        35                  40                  45

Asn Tyr Glu Gly Trp Asn Leu Trp Val Trp Gly Thr Gly Val Lys Asp
    50                  55                  60

Asp Gln Ile Asp Phe Thr Glu Phe Lys Glu Gly Lys Ala Tyr Ala Asp
65                  70                  75                  80

Ile Ala Val Ser Asp Asn Ala Asp Lys Val Gly Phe Ile Ile Arg Lys
                85                  90                  95

Gly Asp Trp Glu Glu Lys Asp Phe Asp Gly Asp Arg Ser Ile Thr Ile
            100                 105                 110

Asn Lys Ile Asp Asn Ile Thr Lys Val His Val Thr Ser Gln Gln Glu
        115                 120                 125

Lys Phe Gly Gln Ile Pro Asp Gly Ser Pro Val Val Ala Asp Gly
    130                 135                 140

Asn Ala Asp Phe Phe Phe Arg Asp Lys Glu Leu Tyr Ala Ala Gly Glu
145                 150                 155                 160

Met Asp Lys Val Glu Lys Val Glu Leu Ser Ile Leu Gly Lys Tyr
                165                 170                 175

Glu Met Asn Gly Glu Pro Glu Lys Glu Arg Phe Thr Tyr Thr Leu Ser
            180                 185                 190

Asp Leu Pro Thr Gly Glu His Glu Tyr Thr Tyr Leu Val Thr Val Asp
        195                 200                 205

Gly Gln Thr Glu Glu Val Thr Asp Pro Tyr Asn Thr Val Asp Gly Arg
```

-continued

```
            210                 215                 220
Ser Val Val Glu Tyr Val Thr Ser Asp Val Gln Val Ser Ala Ser Phe
225                 230                 235                 240

Ile Pro Ala Lys Val Asp Tyr Asn Gln Asn Ala Val Val Lys Val Asp
                245                 250                 255

Ile Glu Ser Glu Thr Glu Thr Lys Ile Arg Glu Met Ser Ile Asn Leu
                260                 265                 270

Ser Glu Ile Gly Gly Lys Glu Lys Ala Thr Ile Asp Pro Ala Leu Asn
                275                 280                 285

Glu Leu Thr Val Ala Val Lys Gln Gly Val Thr Ala Gly Val Lys Asn
                290                 295                 300

Leu Pro Ile Thr Ala Ile Asp Glu Phe Gly Asn Arg His Glu Gly Ser
305                 310                 315                 320

Ala Thr Leu Glu Val Gln Ala Arg Thr Ile Thr Gly Glu Lys Ala Asp
                325                 330                 335

Phe Asp Trp Asp Gln Ser Val Val Tyr Phe Met Leu Thr Asp Arg Phe
                340                 345                 350

Phe Asp Gly Asp Ser Ser Asn Asn Asp Pro His Gly Ile Gly Tyr Asp
                355                 360                 365

Thr Ser Lys Ser Gly Thr Tyr Gln Gly Gly Asp Phe Lys Gly Ile Thr
                370                 375                 380

Gln Arg Leu Asp Tyr Leu Asp Glu Leu Gly Ile Asn Thr Ile Trp Ile
385                 390                 395                 400

Ser Pro Val Val Asp Asn Ile Lys Phe Asp Val Arg His Ser Glu Gly
                405                 410                 415

Pro Asp Thr Pro Tyr Tyr Ala Tyr His Gly Tyr Trp Ala Asp Asn Phe
                420                 425                 430

Gly Glu Leu Asn Pro His Phe Gly Ser Met Ala Asp Phe His Glu Met
                435                 440                 445

Ile Asp Ala Ala His Glu Arg Gly Ile Lys Ile Met Val Asp Val Val
450                 455                 460

Leu Asn His Thr Gly Tyr Gly Leu Lys Pro Gly Asp Ser Ser Ser Val
465                 470                 475                 480

Ala Asn Phe Pro Thr Asp Glu Asp Arg Ala Arg Phe Asp Gly Met Leu
                485                 490                 495

Arg Asp Gly Gly Ser Gly Glu Val Arg Gly Glu Leu Ala Gly Leu Pro
                500                 505                 510

Asp Phe Leu Thr Glu Asn Pro Asp Val Arg Glu Gln Val Val Gln Trp
                515                 520                 525

Gln Thr Asp Trp Ile Glu Lys Ser Arg Thr Ala Lys Gly Asn Thr Ile
                530                 535                 540

Asp Tyr Phe Arg Val Asp Thr Val Lys His Val Glu Asp Thr Thr Trp
545                 550                 555                 560

Met Ala Phe Lys Asn Ala Leu Thr Lys Ala Met Pro Glu His Lys Leu
                565                 570                 575

Ile Gly Glu Ala Trp Gly Ala Asn Val Asn Asp Asp Leu Gly Tyr Leu
                580                 585                 590

Asn Ser Gly Met Met Asp Ser Leu Leu Asp Phe Asp Phe Lys Asn Tyr
                595                 600                 605

Ala Arg Asp Phe Ala Asn Gly Gln Leu Asp Ala Val Gln Gln Lys Leu
                610                 615                 620

Glu Ala Arg Asn Ser Lys Leu Asn Asn Thr Ala Thr Leu Gly Gln Phe
625                 630                 635                 640
```

-continued

```
Leu Gly Ser His Asp Glu Asp Arg Phe Tyr Glu Val Glu Gly Asp
            645                 650                 655

Leu Gly Lys Tyr Gln Val Ala Ala Ser Leu Gln Leu Thr Ala Lys Gly
            660                 665                 670

Gln Pro Val Ile Tyr Tyr Gly Glu Leu Gly Leu Pro Gly Lys Asn
            675                 680                 685

Asp Tyr Pro Tyr Tyr Thr Asn Arg Gln Asn Met Pro Trp Asp Val
    690                 695                 700

Asp Gly Asn Glu Ile Leu Glu His Tyr Gln Lys Leu Leu Ala Phe Arg
705                 710                 715                 720

Asn Asp Asn Pro Asn Thr Phe Ala Lys Gly Asp Arg Lys Val Ala
            725                 730                 735

Gly Ser Asp Ser Glu Gly Tyr Leu Leu Phe Ser Arg Thr Tyr Gly Glu
            740                 745                 750

Asn Ser Val Tyr Val Gly Leu Asn Thr Glu Ala Ala Lys Asp Val
            755                 760                 765

Thr Leu Asn Phe Gly Ser Ser Glu Ala Val Thr Asp Arg Tyr Ser
    770                 775                 780

Gly Gln Glu Tyr Gln Ala Asn Glu Gly Gln Val Thr Phe Ser Ile
785                 790                 795                 800

Pro Ala Met Glu Asp Gly Gly Thr Val Leu Leu Glu Val Glu Asn Gly
            805                 810                 815

Ala Val Pro Val Glu Glu Pro Thr Glu Pro Gly Glu Ile Glu
            820                 825                 830

Glu

<210> SEQ ID NO 4
<211> LENGTH: 893
<212> TYPE: PRT
<213> ORGANISM: Bacillus sp.

<400> SEQUENCE: 4

Thr Val Pro Leu Ala Leu Val Ser Gly Glu Val Leu Ser Asp Lys Leu
1               5                   10                  15

Ile Ser Leu Thr Phe Thr Arg Thr Glu Gly Leu Asp Leu Glu Glu Leu
                20                  25                  30

Lys Glu Gln Leu Glu Ile Lys Asp Val Asp Gly Asn Asp Val Ser Phe
            35                  40                  45

Thr Asp Val Thr Ile Glu Gly Glu Lys Thr Val His Val His Gly Glu
    50                  55                  60

Phe Asp Leu Glu Lys Ile Pro Phe Ser Val Thr Tyr Leu Asp Arg Thr
65                  70                  75                  80

Ile Ser Val Lys Ser Gly Trp Lys Leu Ile Asp Glu Met Tyr Ala Tyr
                85                  90                  95

Asp Gly Lys Leu Gly Ala Glu Leu His Glu Asp Gly Thr Ala Thr Leu
            100                 105                 110

Lys Val Trp Ser Pro Lys Ala Asp Asn Val Ser Val Leu Tyr Asp
            115                 120                 125

Lys Val Asp Gln Asn Glu Val Val Asp Thr Ile Glu Met Val Lys Gly
    130                 135                 140

Asp Arg Gly Val Trp Ser Val Lys Leu Thr Lys Asp Asn Thr Gly Leu
145                 150                 155                 160

Asp Ser Leu Lys Gly Tyr Tyr His Tyr Glu Ile Thr His Gly Asp
            165                 170                 175
```

-continued

```
Val Thr Asn Leu Ala Leu Asp Pro Tyr Ala Lys Ser Met Ala Ala Trp
            180                 185                 190
Asn Asn Glu Ala Gly Asp Lys Val Gly Lys Ala Ala Ile Val Asp Ile
            195                 200                 205
Gly Ser Ile Gly Pro Glu Leu Asp Tyr Ala Asp Ile Pro Gly Phe Glu
            210                 215                 220
Lys Arg Glu Asp Thr Ile Ile Tyr Glu Val His Val Arg Asp Phe Thr
225                 230                 235                 240
Ser Asp Pro Asn Ile Gly Glu Asp Leu Lys Ala Gln Phe Gly Thr Phe
            245                 250                 255
Ala Ser Phe Val Glu Lys Leu Asp Tyr Ile Gln Glu Leu Gly Val Thr
            260                 265                 270
His Ile Gln Leu Leu Pro Val Met Ser Tyr Tyr Phe Ser Asn Glu Phe
            275                 280                 285
Glu Ser Gly Glu Arg Met Leu Glu Tyr Ala Ser Thr Gly Thr Asn Tyr
            290                 295                 300
Asn Trp Gly Tyr Asp Pro His Asn Tyr Phe Ser Leu Ser Gly Met Tyr
305                 310                 315                 320
Ser Glu Asn Pro Glu Asp Pro Glu Leu Arg Ile Lys Glu Phe Lys Asn
            325                 330                 335
Leu Ile Asn Glu Ile His Lys Arg Asp Met Gly Val Val Leu Asp Val
            340                 345                 350
Val Phe Asn His Thr Ala Gln Val His Ile Phe Glu Asp Leu Val Pro
            355                 360                 365
Asn Tyr Tyr His Phe Met Asp Ala Asp Gly Thr Pro Arg Thr Ser Phe
            370                 375                 380
Gly Gly Gly Arg Leu Gly Thr Thr His Glu Met Ser Arg Arg Val Leu
385                 390                 395                 400
Val Asp Ser Ile Lys His Trp Val Asp Glu Tyr Lys Val Asp Gly Phe
            405                 410                 415
Arg Phe Asp Met Met Gly Asp His Asp Ala Glu Ser Ile Gln Ile Ala
            420                 425                 430
Phe Asp Glu Ala Lys Lys Leu Asn Pro Asn Ile Val Met Ile Gly Glu
            435                 440                 445
Gly Trp Val Thr Phe Ala Gly Asp Glu Gly Glu Pro Val Gln Ala Ala
            450                 455                 460
Asp Gln Gln Trp Met Gln Tyr Thr Glu Ala Val Gly Ser Phe Ser Asp
465                 470                 475                 480
Glu Phe Arg Asn Glu Leu Lys Ser Gly Phe Gly Ser Glu Gly Gln Pro
            485                 490                 495
Arg Phe Ile Thr Gly Gly Ala Val Asn Val Gln Gln Ile Phe Asp Asn
            500                 505                 510
Ile Lys Ala Gln Pro His Asn Phe Met Ala Asp Gln Pro Gly Asp Val
            515                 520                 525
Val Gln Tyr Ile Glu Ala His Asp Asn Leu Thr Leu Tyr Asp Val Ile
            530                 535                 540
Ala Gln Ser Ile Lys Lys Asp Pro Glu Ile Ala Glu Asn Asp Leu Glu
545                 550                 555                 560
Ile His Lys Arg Ile Arg Val Gly Asn Ala Met Val Leu Thr Ser Gln
            565                 570                 575
Gly Thr Ala Phe Leu His Ala Gly Gln Glu Phe Gly Arg Thr Lys Gln
            580                 585                 590
```

-continued

Trp Arg Ala Pro Ala Thr Glu Ala Pro Tyr Lys Ser Thr Tyr Met Thr
            595                 600                 605

Asp Ala Asp Gly Asn Pro Phe Val Tyr Pro Tyr Phe Ile His Asp Ser
            610                 615                 620

Tyr Asp Ser Ser Asp Ile Ile Asn Arg Phe Asp Trp Glu Lys Ala Thr
625                 630                 635                 640

Asp Ala Glu Lys Tyr Pro Val Asn Asn Val Thr Arg Asp Tyr Thr Ala
            645                 650                 655

Gly Leu Ile Glu Leu Arg Arg Ser Ser Asp Ala Phe Arg Leu Gly Ser
            660                 665                 670

Arg Glu Leu Val Asp Ser Asn Val Thr Met Val Asp Ala Pro Glu Ile
            675                 680                 685

Lys Glu Gln Asp Leu Val Val Ala Tyr Arg Ser Val Ser Thr Ala Gly
            690                 695                 700

Val Glu Tyr Tyr Thr Phe Val Asn Ala Asp Thr Ser Ser Arg Thr Leu
705                 710                 715                 720

Thr Leu Gly Gln Asp Leu Thr Glu Gly Val Val Val Asp Ala Glu
            725                 730                 735

Glu Ala Asn Val Ala Gly Val Ala Glu Pro Ala Gly Phe Glu Leu Thr
            740                 745                 750

Ala Glu Gly Ile Thr Leu Glu Pro Leu Thr Thr Val Val Arg Val
            755                 760                 765

Gly Glu Gln Glu Gly Thr Asp Pro Gly Asp Gly Asp Gly Asp Gly Asn
            770                 775                 780

Thr Pro Pro Pro Gly Asp Gly Asp Gly Asn Thr Pro Pro Pro
785                 790                 795                 800

Gly Asp Gly Asp Gly Asp Gly Asn Thr Pro Pro Gly Asn Gly Asn
            805                 810                 815

Gly Asn Asn Pro Gly Thr Pro Pro Gly Lys Gly Glu Asn Pro Gly
            820                 825                 830

Lys Gly Lys Asn Asp Lys Thr Pro Pro Gly Lys Gly Asp Asn Pro
            835                 840                 845

Gly Lys Gly Asn Lys Leu Pro Leu Thr Ala Thr Gly Thr Leu Asn Tyr
            850                 855                 860

Ile Leu Phe Gly Ala Ile Met Leu Val Leu Gly Thr Leu Leu Tyr Leu
865                 870                 875                 880

Gly Val Arg Arg Lys Ala Gly Leu Lys Glu Lys Thr Leu
                885                 890

<210> SEQ ID NO 5
<211> LENGTH: 16
<212> TYPE: PRT
<213> ORGANISM: Bacillus sp.

<400> SEQUENCE: 5

Thr Val Pro Leu Ala Leu Val Ser Gly Glu Val Leu Ser Asp Lys Leu
1               5                   10                  15

<210> SEQ ID NO 6
<211> LENGTH: 14
<212> TYPE: PRT
<213> ORGANISM: Bacillus sp.

<400> SEQUENCE: 6

Glu Thr Gly Asp Lys Arg Ile Glu Phe Ser Tyr Glu Arg Pro
1               5                   10

```
<210> SEQ ID NO 7
<211> LENGTH: 24
<212> TYPE: DNA
<213> ORGANISM: Artificial Sequence
<220> FEATURE:
<223> OTHER INFORMATION: Primer 1.  Directed to Bacillius sp. used
      between PstI site to the XbaI site.

<400> SEQUENCE: 7
ctgcaggtat cggtaaatac ggtg                                              24

<210> SEQ ID NO 8
<211> LENGTH: 24
<212> TYPE: DNA
<213> ORGANISM: Artificial Sequence
<220> FEATURE:
<223> OTHER INFORMATION: Primer 2.  Directed to Bacillius sp. used
      between PstI site to the XbaI site.

<400> SEQUENCE: 8
tgacgtaacg aatcttgctc taga                                              24

<210> SEQ ID NO 9
<211> LENGTH: 24
<212> TYPE: DNA
<213> ORGANISM: Artificial Sequence
<220> FEATURE:
<223> OTHER INFORMATION: Primer 3. Directed to Bacillius sp. used
      between XbaI to 1.2 kb upstream.

<400> SEQUENCE: 9
tctagagcat tatcaaaaat tact                                              24

<210> SEQ ID NO 10
<211> LENGTH: 24
<212> TYPE: DNA
<213> ORGANISM: Artificial Sequence
<220> FEATURE:
<223> OTHER INFORMATION: Primer 4. Directed to Bacillius sp. used
      between XbaI to 1.2 kb upstream.

<400> SEQUENCE: 10
ccggaactga gaatcaaaga attc                                              24

<210> SEQ ID NO 11
<211> LENGTH: 24
<212> TYPE: DNA
<213> ORGANISM: Artificial Sequence
<220> FEATURE:
<223> OTHER INFORMATION: Primer 5.  Directed to Bacillus sp. EcoRI
      site to 1.1 kb upstream.

<400> SEQUENCE: 11
gaattcggaa atcgccatga ggga                                              24

<210> SEQ ID NO 12
<211> LENGTH: 23
<212> TYPE: DNA
<213> ORGANISM: Artificial Sequence
<220> FEATURE:
<223> OTHER INFORMATION: Primer 6.  Directed to Bacillus sp. EcoRI
      site to 1.1 kb upstream.

<400> SEQUENCE: 12
gtggatggta atgaaattct aga                                               23
```

```
<210> SEQ ID NO 13
<211> LENGTH: 25
<212> TYPE: DNA
<213> ORGANISM: Artificial Sequence
<220> FEATURE:
<223> OTHER INFORMATION: Primer A. Directed to alkaline
      amylopullulanase gene.

<400> SEQUENCE: 13
tctagatgtg caattttgcg caaac                                    25

<210> SEQ ID NO 14
<211> LENGTH: 25
<212> TYPE: DNA
<213> ORGANISM: Artificial Sequence
<220> FEATURE:
<223> OTHER INFORMATION: Primer B. Directed to alkaline
      amylopullulanase gene.

<400> SEQUENCE: 14
aagcttgggg cagaattgca tgaag                                    25
```

GENE FOR ENZYME HAVING BOTH ALKALINE PULLULANASE AND ALKALINE ALPHA-AMYLASE ACTIVITIES

This is a divisional of application Ser. No. 09/514,302, filed Feb. 28, 2000, now U.S. Pat. No. 6,338,959, the entire contents of which is hereby incorporated by reference, which is a divisional of application Ser. No. 08/952,084, filed Nov. 10, 1997, now abandoned, which is a 371 of PCT/JP96/01243, filed May 10, 1996, which claims priority of Application No. 111547 filed in Japan on May 10, 1995 under U.S.C. §119.

TECHNICAL FIELD

The present invention relates to the gene encoding an enzyme that exhibits both alkaline pullulanase activity and alkaline α-amylase activity (alkaline amylopullulanase), to alkaline α-amylase and alkaline pullulanase obtainable from expression of a fragment of the gene encoding the intact alkaline amylopullulanase, to the gene or fragments thereof encoding these enzymatic activities, and to recombinant DNAs and transformants bearing the gene and fragments thereof.

BACKGROUND ART

Alpha-amylase has long been used in a variety of fields. For example, it has been used for the saccharification of grains and potatoes in the fermentation industry, as starch paste removers in the textile industry, as digestives in the pharmaceutical industry, and for the manufacture of thick malt sugar syrups in the food industry. Alpha-amylase is an enzyme which acts on starch-related polysaccharides such as amylose or amylopectin, cutting solely the α-1,4-glucoside bond of the polysaccharide molecule. Crystalline samples or electrophoretically uniform samples of α-amylase have been obtained from a number of different sources including bacteria, fungi, plant seeds, and animal digestive glands. Pullulanase is an enzyme which hydrolyzes solely the α-1, 6-glucoside bond present in starch, glycogen, amylopectin, and pullulan. Pullulanase was first found in a certain strain of *Aerobacter aerogenes* (Bender, H. and Wallenfels, K., *Biochem. J.*, 334, 79 (1961)), and thereafter, was also found in many other microorganisms including genera Bacillus, Streptococcus and Clostridium. Pullulanase has become of interest in the starch-making industry because of its ability to produce, from starch, maltooligosaccharides such as glucose, maltose, maltotriose, maltopentaose, and maltohexaose when it is used in combination with endo-type amylase and exo-type amylase.

In order to simplify the process of the manufacture of saccharides in which two or more enzymes are used, as described above, pullulanase which also acts on the α-1,4-glucoside bond, in other words, pullulanase exhibiting α-amylase activity, is greatly desired. *Bacillus subtilis* TU strain is known to produce a pullulanase-amylase complex enzyme (Takasaki, Y., *Agric. Biol. Chem.*, 51, 9 (1987), Japanese Patent Publication (kokoku) No. 1-18717). In addition, enzymes exhibiting the above two distinct enzymatic activities or so-called amylopullulanases have been reported for a number of bacteria including Bacillus circulans (Japanese Patent Application Laid-open (kokai) No. 64-60376), Bacillus sp. (Saha, B. C., et al., *Enzyme Microb. Technol.*, 11, 760 (1989)), *Thermoanaerobium brockii* (Coleman, R. D. et al., *J. Bacteriol.*, 169, 4302 (1987)), Thermoanaerobium sp. (Plant, A. R., et al., *Appl. Microbiol. Biotechnol.*, 26, 427 (1987)), *Clostridium thermohydrosulfuricum* (Saha, B. C., et al., *Biochem. J.*, 252, 343 (1988)), *Clostridium thermosulfurogenes* (Spreinat, A. et al., *Appl. Microbiol. Biotechnol.*, 33, 511 (1990)), *Thermus aquaticus* (Plant, A. R., et al., *Enzyme Microb. Technol.*, 8, 668 (1986)), Thermus sp. (Nakamura, N et al., Starch/Starke, 41, 112 (1989)), *Thermoanaerobacterium saccharolyticum* (Saha, B. C., et al., *Appl. Environ. Microbiol.*, 56, 881 (1990)), and *Pyrococcus furiosus* and *Thermococcus litoralis* (Brown, S. H. and Kelley, R. M., *Appl. Environ. Microbiol.*, 59, 2614 (1993)).

The present inventors have recently discovered that the efficacy of dish-washing detergents and detergents for clothes can be greatly improved, particularly on starch soils, when α-amylase and pullulanase are both incorporated into the detergents (Japanese Patent Application Laid-open (kokai) No. 2-132193). However, most of the α-amylases and pullulanases previously found in the natural world exhibit maximal and stable enzymatic activities in the neutral to acidic pH ranges, but scarcely work in an alkaline solution of pH 9–10. There exist very few enzymes exhibiting maximal activities in the alkaline pH range (alkaline pullulanases), and only two reports of such enzymes have been published (Nakamura, N. and Horikoshi, K., *Biochim. Bophys. Acta*, 397, 188 (1975), Japanese Patent Publication (kokoku) No. 53-27786 and Ara et al. Japanese Patent Publication (kokoku) No. 6-32613. Furthermore, an enzyme that has both alkaline α-amylase and alkaline pullulanase activities had not been reported until the present inventors discovered that an alkalophilic Bacillus sp. KSM-AP1378 (FERM BP-3048, deposited Jul. 24, 1989 in Fermentation Research Institute, Agency of Industrial Science and Technology of 1–3, Higashi 1-chome, Tsukuba-shi, Ibaraki, 305 Japan) having its optimum pH for growth in the alkaline range produces a novel alkaline amylopullulanase (formerly designated pullulanase Y) that has both alkaline pullulanase and alkaline α-amylase activities. They elucidated that this enzyme is useful as an additive in detergent compositions for automatic dishwashers and in detergent compositions for clothes (Japanese Patent Application Laid-open (kokai) No. 3-290498). Although this enzyme is constituted by a single enzyme molecule, it exhibits both alkaline α-amylase activity and alkaline pullulanase activity. Exploitation of this enzyme has proved very advantageous in culturing the bacteria and in purification of the enzyme, compared to the case in which the two enzymes are independently produced by two different bacteria.

The present inventors have attempted to improve productivity of the alkaline amylopullulanase (formerly designated pullulanase Y) producing bacterium, Bacillus sp. KSM-AP1378, through optimization of culturing methods. Nevertheless, it is still desired to improve further the enzyme productivity of the bacterium so as to advantageously produce the alkaline amylopullulanase on an industrial scale. It is noted that production of the enzyme can be further enhanced using genetic engineering and the activity of the enzyme itself can be improved by altering the gene encoding the enzyme using a protein engineering approach. Applying these approaches requires the gene encoding alkaline amylopullulanase.

Accordingly, an object of the present invention is to provide the gene encoding alkaline amylopullulanase, recombinant DNA comprising the gene, and a transformant harboring the recombinant DNA.

The DNA encoding the alkaline amylopullulanase gene may be further used to produce probes to be used in the isolation of additional, homologous alkaline amylopullulanase genes from other microorganisms. Thus, an additional object of the present invention is to provide a means of screening for and isolating additional alkaline amylopullulanase enzymes.

DISCLOSURE OF THE INVENTION

The present inventors isolated a DNA fragment encoding alkaline amylopullulanase from the chromosomal DNA of an alkalophilic Bacillus strain using shotgun cloning and PCR. When they transformed a microorganism with this DNA fragment ligated to a suitable vector, it was confirmed that the resultant recombinant microorganism produced alkaline amylopullulanase. Moreover, it was found that the amino acid sequence of the alkaline amylopullulanase encoded by the DNA fragment is completely different from those of previously known amylases and pullulanases, and that this enzyme has the feature that the amino terminal moiety of the enzyme molecule is alkaline α-amylase, and the carboxy terminal moiety of the enzyme molecule is alkaline pullulanase. The present invention was accomplished based on this finding.

Accordingly, the present invention provides a DNA fragment encoding alkaline amylopullulanase.

The present invention also provides alkaline α-amylase having the amino acid sequence described in SEQ ID NO:3 provided hereinbelow, as well as a DNA fragment encoding he alkaline α-amylase.

The present invention also provides alkaline pullulanase having the amino acid sequence described in SEQ D NO:4 provided hereinbelow, as well as a DNA fragment encoding the alkaline pullulanase.

The present invention also provides recombinant DNA comprising a DNA fragment encoding the above-described alkaline amylopullulanase, alkaline α-amylase, or alkaline pullulanase.

The present invention also provides a transformed microorganism harboring recombinant DNA comprising a DNA fragment encoding the above-described alkaline amylopullulanase, alkaline α-amylase, or alkaline pullulanase.

The present invention further provides a method for producing alkaline amylopullulanase, alkaline α-amylase, or alkaline pullulanase, characterized by culturing the above-described transformed microorganism and collecting any one of the expressed enzymes.

BRIEF DESCRIPTION OF THE DRAWINGS

FIG. 6 shows nucleotide sequences of prime s used for PCR (SEQ ID NOS:7 to 14). Primers 1 (SEQ ID NO:7), 3 (SEQ ID NO:9), 5 (SEQ ID NO:11) and B (SEQ ID NO:14) were used as complementary sequences.

DETAILED DESCRIPTION OF THE PREFERRED EMBODIMENTS

Figure 1:
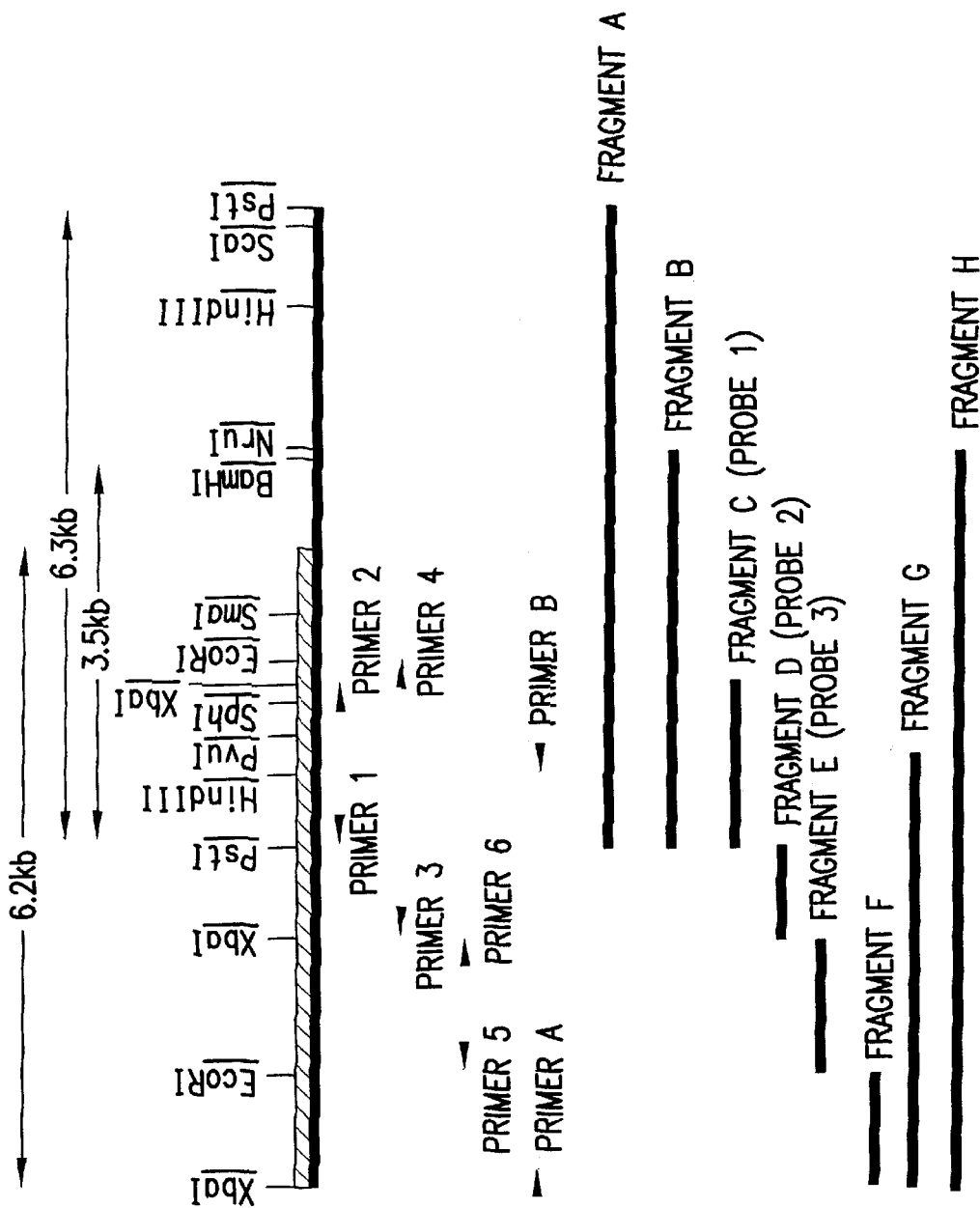
FIG. 1 shows a restriction enzyme map of the alkaline amylopullulanase gene from Bacillus sp. KSM-AP1378 and positions of the primers.

In the present invention, a useful microorganism which serves as an alkaline amylopullulanase gene donor may be, for example, Bacillus sp. KSM-AP1378, which is an alkalophilic Bacillus. This strain was isolated from the soil in the vicinity of the city of Tochigi in Tochigi Prefecture, Japan by the present inventors and identified as a strain producing significant amounts of alkaline amylopullulanase. This strain has been deposited at the Fermentation Research Institute under BP-3048.

In order to obtain chromosomal DNA from a donor microorganism, methods proposed by Marmur, J. (*J. Mol. Biol.*, 3, 208 (1961)) and by Saito, H. and Miura, K. (*Biochim. Biophys. Acta*, 72, 619 (1963)) may be used. Other similar methods may also be used.

DNA fragments comprising the alkaline amylopullulanase gene are prepared by cleaving the thus-obtained chromosomal DNA using restriction enzymes. Restriction enzymes which may be used are not particularly limited so long as they do not damage the gene. The alkaline amylopullulanase gene may also be obtained by PCR. For example, the gene may be obtained by synthesizing primers having sequences corresponding to those on the upstream side of the 5'-terminus and on the downstream side of the 3'-terminus of the essential region based on the nucleotide sequence described in SEQ ID NO:1, and conducting PCR using, as a template, the chromosomal DNA of an alkaline amylopullulanase-producing microorganism. Alternatively, an intact gene may be obtained by either method of first obtaining an alkaline pullulanase gene fragment from an alkaline amylopullulanase-producing microorganism using any procedure, followed by PCR which amplifies an alkaline α-amylase gene fragment existing on the upstream side of the former fragment, or conversely, via a method of first obtaining an alkaline α-amylase gene, followed by PCR which amplifies an alkaline pullulanase gene fragment existing on the downstream side of the gene.

The thus-prepared genetic fragment is then subjected to cloning. Host/vector systems which may be used are not particularly limited, so far as host bacterial strains express the alkaline amylopullulanase gene of the present invention, that the recombinant DNA can be replicated in the host bacteria, and that the recombinant DNA can stably harbor the integrated gene. For example, members of the EK system in which the host is *E. coli* K-12, and those of the BS system in which the host is *Bacillus subtilis* Marburg may be used. Use of the EK system which encompasses many kinds of vectors and is extensively studied genetically provides good results and thus is preferred. Specific examples of host bacteria include strains HB101, C600, and JM109 of the EK system, and strains BD170, MI11, and ISW1214 of the BS system. Specific examples of vectors include pBR322 and pUC18 of the EK system, and pUB110 and pHY300PLK of the BS system. A recombinant plasmid DNA is created by cleaving a vector with a restriction enzyme followed by ligation with the above-mentioned chromosomal or PCR-amplified DNA fragment. The ligation may be achieved, for example, through the use of a DNA ligase.

Methods for transforming host bacterial strains using recombinant DNA are not particularly limited. For example, a calcium chloride method (Mandel, M. and Higa, A., *J. Mol. Biol.*, 53, 159 (1970)) may be used in the case of hosts of the EK system, and a protoplast method (Chang, C. and Cohen, S. N., *Mol. Gen. Genet.*, 168, 111 (1978)) may be used in the case of hosts of the BS system.

Selection of recombinant microorganisms are performed as follows. First, microorganisms which have been transformed with DNA containing a vector-derived DNA fragment are selected using, as an index, a character such as antibiotics resistance coded on the vector DNA which is not inactivated by insertion of exogenous chromosomal or PCR-amplified DNA fragments. For example, in a specific case in which pBR322 of EK system is used as a vector, and a BamHI fragment of chromosomal DNA is inserted into the BamHI cleavage site of pBR322, the tetracycline resistant gene is inactivated, so a primary selection may be conducted using, as an index, ampicillin resistance without having a BamHI cleavage site in the gene. Subsequently, the selected microorganisms are transferred onto agar plates containing starch or pullulan using, for example, a replica method and are then cultured to form colonies. Colonies are detected that decompose starch, that form halos on the starch-containing agar plate, and that also form halos on the pullulan-containing agar plate.

The recombinant DNA harbored by the thus-obtained recombinant microorganism can be extracted using standard procedures for preparing plasmids or phage DNAs (Maniatis, T. et al., *Molecular Cloning*, Cold Spring Harbor Laboratory, New York (1982)). By cleaving the extracted recombinant DNA using a variety of restriction enzymes and analyzing cleavage patterns by electrophoresis, it is confirmed that the recombinant DNA is a ligated product of the vector DNA and a DNA fragment containing the alkaline amylopullulanase gene.

Fragments encoding the alkaline pullulanase activity, parts of the alkaline amylopullulanase of the present invention, are contained in a DNA fragment of about 9.4 kb, as shown in the restriction enzyme map of FIG. 1, and are present in the segment of about 6.2 kb shown by the cross-hatched bar.

The fragment having a size of about 6.2 kb and containing the alkaline amylopullulanase gene has a nucleotide sequence shown by SEQ ID NO:1. In this sequence, the 5' terminus and 3' terminus correspond to the left-hand side and the right-hand side, respectively, of the fragment of about 6.2 kb. In this sequence is observed an open reading frame (ORF) starting translation at the $145^{th}$ ATG and coding for a sequence formed of 938 amino acid residues described SEQ ID NO:2. Fifteen bases (15 b) upstream of the ORF, there exists a sequence GAAAGGGG which is highly complementary to the 340 terminal sequence of the 16S ribosomal RNA of *Bacillus subtilis* (McLaughlin, J. R. et al., *J. Bol. Chem.*, 256, 11283 (1981)). On a further upstream side extending from the $35^{th}$ nucleotide, there exists a sequence TTTACA . . . 20 b . . . TAAATT which has high homology with the consensus sequence of a $\sigma^A$-type promoter (Gitt, M. A. et al, *J. Biol. Chem.*, 26 , 7178 (1985)). On the downstream side of the translation termination condon TAA at the $5959^{th}$ nucleotide, there exists an inverted repeated sequence (nucleotide Nos. 5961–6015) which is presumably a transcription terminator. In addition, the amino acid sequence of the 14 residues on the amino terminus side in alkaline amylopullulanase obtained through purifying a culture of Bacillus sp. KSM-AP1378 coincides with the sequence extending from the first amino acid (amino acids 1–14 in SEQ ID NO:1) deduced from the nucleotide sequence in the DNA fragment.

When the nucleotide sequence of the gene of the present invention and a putative amino acid sequence were compared with those of α-amylase and pullulanase known hitherto, it was confirmed that the present gene is a novel one possessing a unique nucleotide sequence, with the amino acid sequence encoded by the gene being different from that of either α-amylase or pullulanase.

Moreover, the gene of the present invention is characterized in that it encodes an enzyme possessing two active centers, one for alkaline α-amylase and the other for alkaline pullulanase, in a single peptide chain of the protein. There is each of four sequences (regions I–IV; Nakajima, R. et al, *Appl. Microbiol. Biotechnol.*, 23, 355 (1986)) observed uniquely for the active center of amylase, amino acids 430–613, and for pullulanase, amino acids 1364–1549. Specifically, in the amino acid sequence of SEQ ID NO:1, region I of alkaline α-amylase=430–435, region II of alkaline α-amylase=514–522, region III of alkaline α-amylase=547–550, region IV of alkaline α-amylase=608–613, region I of alkaline pullulanase=1363–1369, region II of alkaline pullulanase=1428–1436, region III of alkaline pullulanase=1461–1464, region IV of alkaline pullulanase=1544–1549. Moreover, between the structural genes presumably encoding alkaline α-amylase and alkaline pullulanase, respectively, an intervening sequence formed of 33 amino acids appears twice (in the amino acid of SEQ ID NO:1, 802–834 and 912–944). Therefore, by using this characteristic feature, it is also possible to express the alkaline α-amylase moiety and the alkaline pullulanase moiety in an independent manner. For example, if a gene encoding the amino acids stretching from the initiation codon to directly before the intervening sequence is inserted into a plasmid vector DNA and is introduced into a suitable host bacterium, it is possible to produce alkaline α-amylase alone (SEQ ID NO:3). Likewise, if a gene containing the amino acids stretching directly after the intervening sequence to the $1906^{th}$ amino acid is inserted into a plasmid vector DNA and is introduced into a suitable host bacterium, it is possible to produce alkaline pullulanase alone (SEQ ID NO:4).

Figure 2:
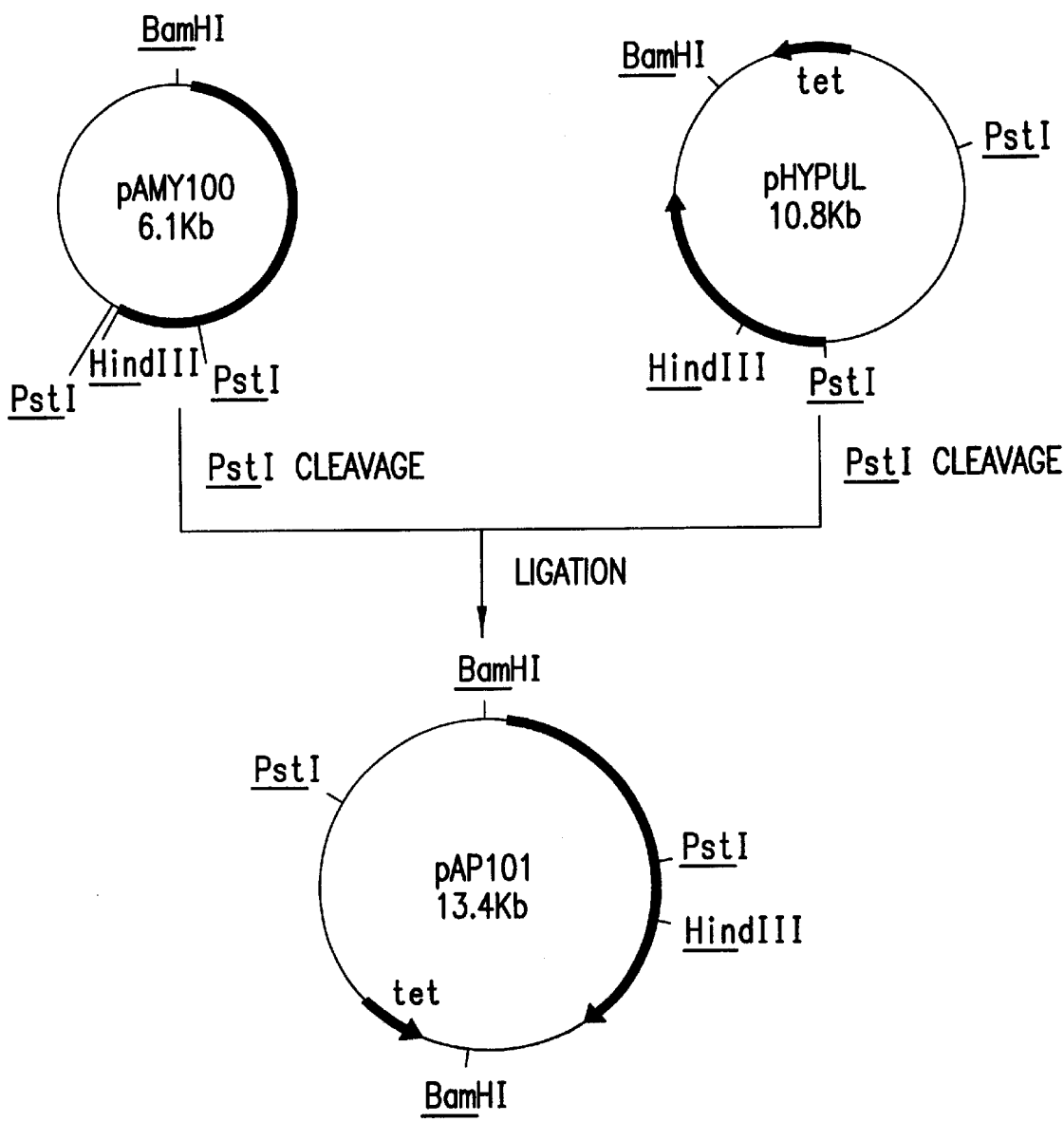
FIG. 2 is a scheme of subcloning of the alkaline amylopullulanase gene from Bacillus sp. KSM-AP1378.
Figure 3:
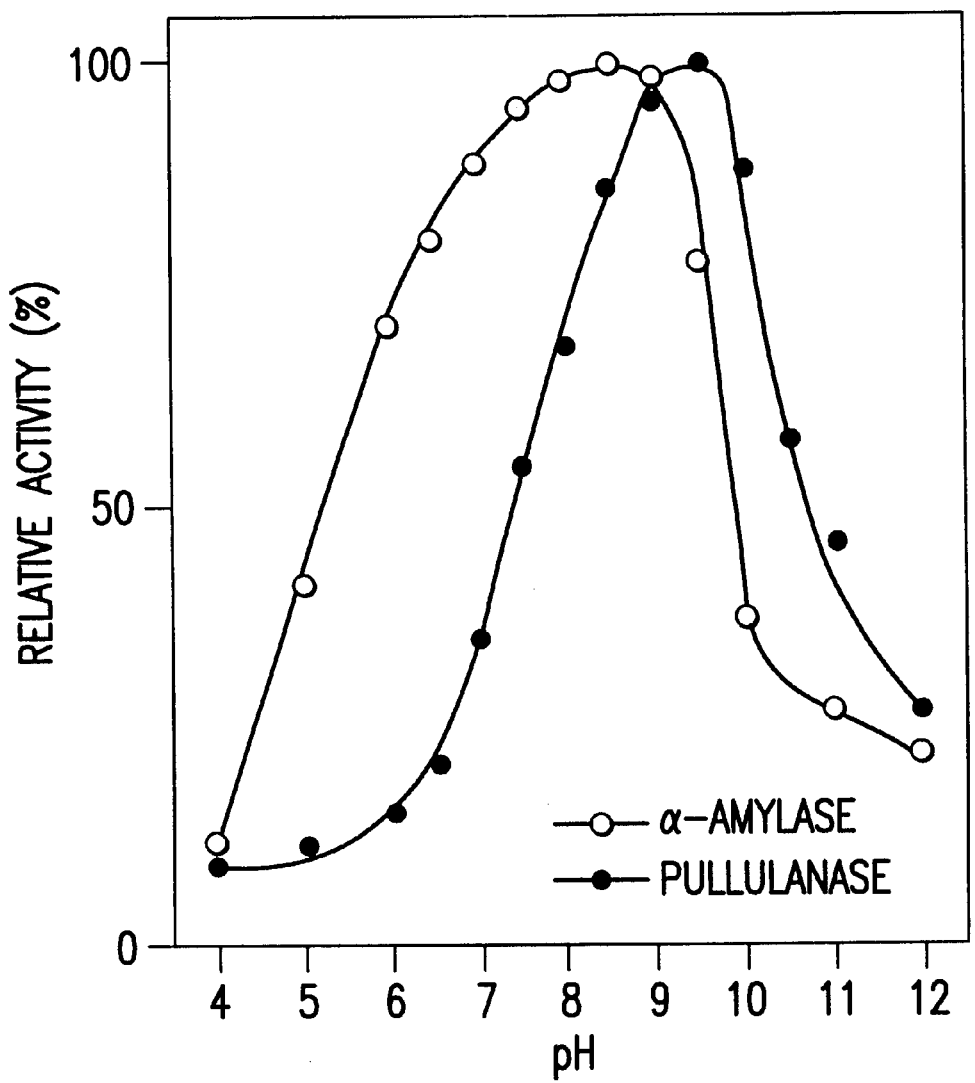
FIG. 3 is a graph showing the pH profiles of α-amylase activity and pullulanase activity of alkaline amylopullulanase.

An example of a preferred recombinant DNA containing the entire region of the alkaline amylopullulanase gene is plasmid pAP101 (FIG. 2). This plasmid has a size of 13.4 kb and is of a fragment containing the 6.2 kb alkaline amylopullulanase gene and part of pHY300PLK and pUC18. An example of a preferred recombinant microorganism harboring the recombinant DNA is an E. coli HB101(pAP101) strain. This strain is a product obtained by transforming E. coli HB101 strain with a recombinant plasmid, pAP101, using a standard transformation method. When this strain is cultured using a medium routinely employed for culturing E. coli, it produces alkaline amylopullulanase. The optimum reaction pHs of the thus-produced enzyme are pH 8–9 for the α-amylase activity and pH 9–10 for the pullulanase activity. This agrees well with the activity-pH relationship profiles determined for alkaline amylopullulanase produced by the gene donor bacterium Bacillus sp. KSM-AP1378 (FIG. 3).

The DNA fragments of the present invention are not necessarily limited only to those encoding the amino acid sequences shown in the below-described sequence listing so far as they encode a protein having the enzymatic activity of interest, and they encompass DNA fragments encoding an amino acid sequence in which one or more amino acids are substituted, added, deleted, inverted, or inserted. An example of such DNA is one encoding an amino acid sequence equivalent to the amino acid sequence described in SEQ ID NO:2 from which 32 amino acids on the N-terminal side have been deleted. Thus an alkaline amylopullulanase of SEQ ID NO:2 wherein between 1 to 32 amino acids have been deleted from the amino terminus is encompassed by the present invention.

When the thus-obtained transformants are cultured using known methods, alkaline α-amylase, alkaline pullulanase, or alkaline amylopullulanase can be produced. That is, if a transformant containing a domain encoding only alkaline α-amylase is used, alkaline α-amylase is obtained; if a transformant containing a domain encoding only alkaline pullulanase is used, alkaline pullulanase is obtained; and if a transformant containing a domain coding for the entire alkaline amylopullulanase is used, alkaline amylopullulanase is obtained.

The DNA fragments of the present invention may be further used as probes for the isolation of homologous alkaline amylopullulanase genes from other organisms.

EXAMPLES

The present invention will next be described in more detail by way of examples, which should not be construed as limiting the invention thereto. Concentrations in the Examples are all on a basis of % by weight.

Example 1

Isolation of Chromosomal DNA

Bacillus sp. KSM-AP1378 which produces alkaline amylopullulanase was inoculated into 5 ml of medium A (Table 1) and subjected to shaking culture at 30° C. for 24 hours. One ml of the culture was inoculated in 100 ml of the same medium, followed by shaking culture at 30° C. for a further 12 hours. Subsequently, cells were centrifugally collected and about 1 mg of chromosomal DNA was obtained in accordance with a method proposed by Saito and Miura (Saito, H. and Miura K., Biochim Biophys. Acta, 72, 619 (1963)).

TABLE 1

| Composition of medium A | |
|---|---|
| Pullulan | 1.0% |
| Tryptone | 0.2% |

TABLE 1-continued

| Composition of medium A | |
|---|---|
| Yeast extract | 0.1% |
| $KH_2PO_4$ | 0.03% |
| $(NH_4)_2SO_4$ | 0.1% |
| $MgSO_4.7H_2O$ | 0.02% |
| $CaCl_2.2H_2O$ | 0.02% |
| $FeSO_4.7H_2O$ | 0.001% |
| $MnCl_2.4H_2O$ | 0.0001% |
| $Na_2CO_3$ | 0.5% (separately sterilized) |
| | pH: 10 |

Example 2

Isolation of DNA Fragment Encoding Alkaline Pullulanase

The chromosomal DNA (10 μg) obtained in Example 1 was cleaved using a restriction enzyme PstI, after which a vector plasmid pBR322 (1 μg, Boehringer Mannheim) which had been cleaved likewise with PstI was added and a ligation reaction was caused using T4 DNA ligase, thereby producing a mixture of recombinant plasmids. A suspension of E. coli which had undergone transformation with the recombinant plasmid mixture was spread onto an LB agar plate medium (1.0% tryptone (Difco), 0.5% yeast extract (Difco), 1.0% NaCl, and 1.5% agar (Wako Pure Chemical)) containing 15 μg/ml of tetracycline and cultured at 37° C. for 12 hours. On the colonies of transformed cells which emerged, 0.8% agar containing 0.2% pullulan, 0.8% red pullulan (Kanno, M. and Tomiura, E., Agric. Biol. Chem., 49, 1529 (1985)), 1 mg/ml of lysozyme, and a glycine-NaCl—NaOH buffer (pH 9.0) was overlaid and reaction was caused at 37° C. for 5 hours. As a result, a single strain was obtained which formed a transparent halo around a colony of the strain due to decomposition of red pullulan. This strain was isolated as a recombinant microorganism capable of producing alkaline pullulanase.

Example 3

Restriction Map of Plasmid with Alkaline Pullulanase DNA

The recombinant microorganism obtained in Example 2 was inoculated into 5 ml of an LB medium (1.0% tryptone (Difco), 0.5% yeast extract (Difco), 1.0% NaCl) containing 15 μg/ml of tetracycline and cultured at 37° C. overnight. Thereafter, the culture was transferred into 500 ml of an LB medium, followed by shaking culture for 24 hours. Cells were centrifugally collected from the culture, and about 500 mg of a recombinant plasmid was obtained using a standard method (Maniatis, T. et al., Molecular Cloning, Cold Spring Harbor Laboratory (1982)). From a restriction enzyme map of the resultant recombinant plasmid, it was found that the plasmid contained a PstI fragment (fragment A) of about 6.3 kb, as shown in FIG. 1. This plasmid was named pPU100. The E. coli HB101 strain transformed with the plasmid pPU100 was named HB101(pPU100).

Example 4

Measurement of Alkaline Pullulanase Activity

One ml of a culture of strain HB101(pPU100) which had been cultured overnight using 5 ml of an LB medium (containing tetracycline) was inoculated into 100 ml of an LB medium (containing tetracycline), followed by shaking culture at 37° C. for 24 hours. Subsequently, the cells collected through centrifugal separation were suspended in Tris-HCl buffer (pH 8.0) and the cells were disrupted by sonication. The cell debris was removed by centrifugal separation, and the supernatant was used as a cell-free extract. Similarly, a control cell-free extract was prepared using strain HB100(pBR322). Pullulanase activity of these extracts was measured. The pullulanase activity was measured by first causing a reaction in a reaction mixture containing 40 mM glycine—NaCl—NaOH buffer (pH 10) and pullulan (final concentration=0.25%) at 40° C. for 30 minutes, and the resultant reducing sugar was quantitatively determined by the 3,5-dinitrosalicylic acid (DNS) method (Miller, G. L., et al., Anal. Biochem., 2, 127 (1960)). The amount of enzyme which produces a quantity per minute of reducing sugar equivalent to 1 µmol of glucose is taken as 1 unit. As a result, pullulanase activity was detected in a cell-free extract of strain HB101(pPU100). Further, when the optimum working pH of the produced pullulanase was measured, it was found that the pullulanase was in fact an alkaline pullulanase having the optimum working pH of pH 9.5. For the measurement of enzymatic activity, the following buffers (each at 40 mM) were used:

pH 3.5–5.5: Acetate buffer pH 5.5–8.5: Tris-maleic acid buffer pH 8.5–10.5: Glycine-NaCl—NaOH buffer pH 10.5–11.0: $Na_2CO_3$—$NaHCO_3$ buffer

Example 5

Southern Hybridization of Alkaline Amylopullulanase Gene with PstI Digested Chromosomal DNAs of Bacillus sp. KSM-AP1378

Figure 4:
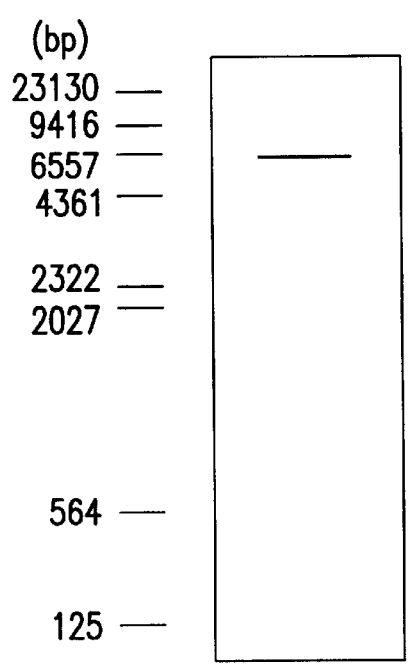
FIG. 4 shows the result of Southern hybridization analysis of PstI digestion products of the chromosomal DNA of a strain KSM-AP1378 from Bacillus sp. KSM-AP1378 using fragment A as a probe. On the left-hand side of the Southern filter, the positions of a size marker for lambda DNA-HindIII digestion products (Boehringer Mannheim) which simultaneously underwent electrophoresis are indicated together with the sizes of the respective DNA fragments.
Figure 5:
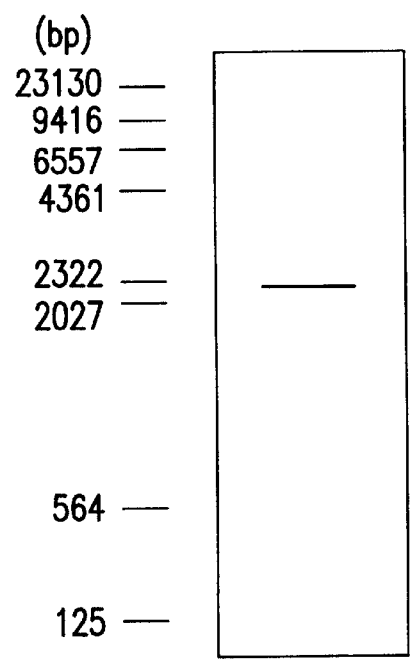
FIG. 5 shows the result of Southern hybridization analysis of XbaI digestion products of the chromosomal DNA of a strain KSM-AP1378 from Bacillus sp. KSM-AP1378 using fragment C as a probe. On the left-hand side of the Southern filter, the positions of a size marker for lambda DNA-HindIII digestion products (Boehringer Mannheim) which simultaneously underwent electrophoresis are indicated together with the sizes of the respective DNA fragments.

About 5 µg of pPU100 was cleaved with a restriction enzyme PstI and was then subjected to electrophoresis on an agarose gel. From the gel, about 0.5 µg of a PstI fragment having a size of about 6.3 kb was isolated using a Geneclean kit (Biolol Inc.). The PstI fragment was labelled using a DNA labelling & detection kit (Boehringer Mannheim) to prepare a probe DNA. Independently, chromosomal DNAS (3 µg each) derived from Bacillus sp. KSM-AP1378 cleaved with PstI were subjected to electrophoresis on an agarose gel, and the DNA bands were transferred onto a nylon membrane (Amersham) using a method proposed by Southern (Southern, E. M., *J. Mol. Biol.*, 98, 503 (1975)). Hybridization with the probe DNA was investigated using a DNA labelling & detection kit. As a result, in PstI cleavage products of chromosomal DNAs derived from the KSM-AP1378 strain, presence of a DNA fragment having a size of about 6.3 kb that hybridized with the probe DNA was detected as shown in FIG. 4. Thus, the PstI fragment having a size of about 6.3 kb contained in plasmid pPU100 was confirmed to be originated from the chromosomal DNA of Bacillus sp. KSM-AP1378.

Example 6

Construction of Plasmid Containing DNA Fragment Encoding Alkaline Pullulanase A recombinant plasmid pHYPUL was created by inserting, between the PstI site and the BamHI site of plasmid pHY300PLK, a fragment having a size of about 3.5 kb (fragment B, FIG. 1) and obtained by cleaving a PstI fragment having a size of about 6.3 kb contained in plasmid pPU100 with BamHI. *E. coli* HB101 was transformed with the thus-created recombinant plasmid, and pullulanase activity was measured through a method similar to that of Example 4. As a result, a pullulanase activity having an optimum working pH in the pH range from 9 to 10 was observed. Thus, the essential domain of alkaline pullulanase was elucidated to be a stretch of about 3.5 kb from the PstI site to the BamHI site.

Example 7

Sequencing of DNA Fragments Encoding Alkaline Pullulanase

Using the fragment B obtained in Example 6, a commercially available deletion kit (Kilosequence Deletion kit, Takara Shuzo), and two suitable restriction enzymes, recombinant plasmid DNAs containing resultant reduced fragments were created, and the nucleotide sequences of the inserted fragments were determined. Nucleotide sequence was determined using a DNA sequencer (Model 370A, Applied Biosystems) and Taq-Dydeoxy Cycle Sequencing kit (Applied Biosystems) in accordance with a method using a fluorescent primer (Smith, L. M., et al., *Nature*, 321, 674 (1986)). By overlapping nucleotide sequences having sizes of about 300–450 bp from respective DNA samples, the 3038 bp sequence on the PstI site side of fragment B was determined. As a result, the open reading frame (ORF) of the alkaline pullulanase gene was found to continue to the upstream side of the PstI site, which is a terminus of the obtained fragment having a size of about 6.3 kb. Restriction Mapping of the Alkaline Amylopullulanase Gene

Example 8

Using a fragment of about 6.3 kb as shown in FIG. 1, a PstI–XbaI 1.5 kb fragment (fragment C) was created, and labeled in a manner similar to that described in Example 5 to prepare a probe DNA (probe 1). Separately, chromosomal DNAs derived from Bacillus sp. KSM-AP1378 which had been cleaved with XbaI (3 µg each) were subjected to electrophoresis on an agarose gel, and the resultant DNA bands were transferred onto a nylon membrane (Amersham) in a manner similar to that described in Example 5, followed by hybridization with the probe. As a result, probe 1 was found to hybridize with an XbaI fragment having a size of a out 2.3 kb, and from this, it was deduced that there exists an XbaI site about 0.8 kb upstream of a 6.3 kb fragment PstI–PstI on the chromosomal DNA derived from the KSM-AP1378 strain (FIG. 1). The stretch from the PstI site to the XbaI site having a length of 0.8 kb was amplified using primer 1 (SEQ ID NO:7) and 2 (SEQ ID NO:8) (FIGS. 1 and 6) each having 24 nucleotides and synthesized based on the nucleotide sequence determined in Example 7, circular DNAs (which were obtained through intramolecular ligation of chromosomal DNA of KSM-AP1378 cleaved with XbaI) which served as templates, and a PCR kit (Applied Biosystems) in accordance with an inverse PCR method (Triglia, T. et al., *Nucleic Acids Res.*, 16, 81 (1988); one cycle=94° C.×1 min.+55° C.×1 mm+72° C.×3 mm., 30 cycles). The sequences of the 0.8 kb fragment (fragment D) which had undergone the above amplification was determined in a manner similar to that described in Example 7. As a result, it was found that the ORF of alkaline pullulanase which continued from fragment C further extended to the upstream of fragment D (FIG. 1).

Example 9

Figure 7:
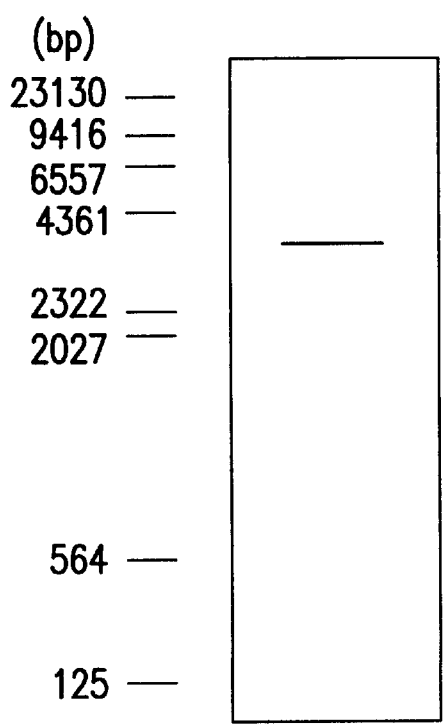
FIG. 7 shows the result of Southern hybridization analysis of EcoRI digestion products of the chromosomal DNA of a strain KSM-AP1378 from Bacillus sp. KSM-AP1378 using fragment D as a probe. On the left-hand side of the Southern filter, the positions of a size marker for lambda DNA-HindIII digestion products (Boehringer Mannheim) which simultaneously underwent electrophoresis are indicated together with the sizes of the respective DNA fragments.

The fragment having a size of about 0.8 kb and stretching from XbaI to PstI obtained in Example 8 was labeled in a manner similar to that described in Example 5 to prepare a probe DNA (probe 2). Separately, chromosomal DNAs derived from Bacillus sp. KSM-AP1378 which had been cleaved with EcoRI (3 μg each) were subjected to electrophoresis on an agarose gel, and the resultant DNA bands were transferred onto a nylon membrane (Amersham) in a manner similar to that described in Example 5, followed by hybridization with probe 2. From the size of a hybridized EcoRI fragment (3.6 kb, FIG. 7), it was deduced that there exists an EcoRI site 1.2 kb upstream of fragment D obtained in Example 8. The stretch from the XbaI site to 1.2 kb upstream of this site was amplified using primers 3 (SEQ ID NO:9) and 4 (SEQ ID NO:10) (FIGS. 1 and 6) having 24 nucleotides and synthesized based on the nucleotide sequence determined in Example 8 and circular DNAs (which were obtained through intramolecular ligation of chromosomal DNA of strain KSM-AP1378 cleaved with EcoRI) which served as template in accordance with an inverse PCR method in a manner similar to that described in Example 8 (fragment E). The sequence of the 1.2 kb fragment which had undergone the above amplification was determined in a manner similar to that described in Example 7. As a result, it was found that the ORF of alkaline pullulanase which continue from fragment D further extended to the upstream of fragment E.

Example 10

Figure 8:
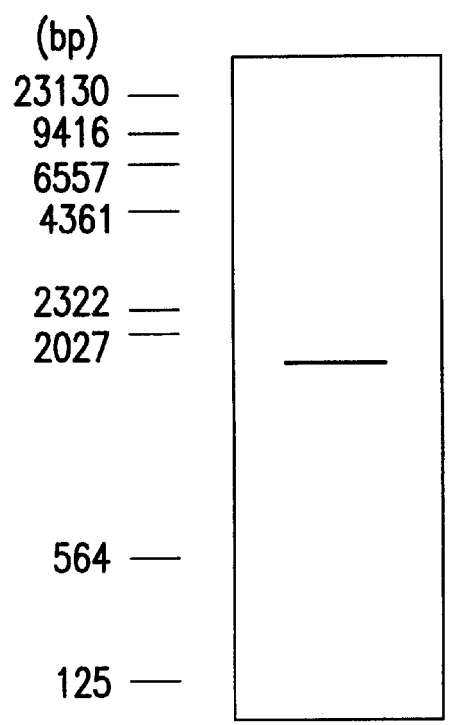
FIG. 8 shows the result of Southern hybridization analysis of XbaI digestion products of the chromosomal DNA of a strain KSM-AP1378 from Bacillus sp. KSM-AP1378 using fragment E as a probe. On the left-hand side of the Southern filter, the positions of a size marker for lambda DNA-HindIII digestion products (Boehringer Mannheim) which simultaneously underwent electrophoresis are indicated together with the sizes of the respective DNA fragments.

The fragment E obtained in Example 9 was a labeled in a manner similar to that described in Example 5 to prepare a probe DNA (probe 3). In a manner similar to Examples 8 and 9, hybridization analysis was performed on XbaI cleavage products of the chromosomal DNA derived from strain KSM-AP1378 (FIG. 8). As a result, as shown in FIG. 1, it was deduced that there exists an XbaI site 1.1 kb upstream of the EcoRI site of fragment D in the chromosomal DNA derived from strain KSM-AP1378. The stretch from the EcoRI site to 1.1 kb upstream of this site was amplified using primers 5 (SEQ ID NO:11) and 6 (SEQ ID NO:12) (FIGS. 1 and 6) each having 24 nucleotides and synthesized based on the nucleotide sequence determined in Example 9 and circular DNAs (which were obtained through intramolecular ligation of chromosomal DNA of strain KSM-AP1378 cleaved with XbaI) which served as templates in accordance with an inverse PCR method in a manner similar to that described in Example 8. The sequence of the 1.1 kb fragment (fragment F) which had undergone the above amplification was determined in a manner similar to that described in Example 7. As a result, it was confirmed that the 5' region of the ORF of alkaline pullulanase gene which continued from fragment E existed in this fragment. The complete nucleotide sequence of the present gene an a deduced amino acid sequence are described in SEQ ID NO:1. Based on the fact that the putative sequence of Nos. 1 through 14 amino acids coincided with the sequence of amino terminus actually determined on Bacillus sp. KSM-AP1378 using alkaline amylopullulanase, it as presumed that the present gene encoded alkaline amylopullulanase.

Example 11

A 3.5 kb fragment (fragment G) containing an alkaline α-amylase domain of the alkaline amylopullulanase gene was amplified using primers A (SEQ ID NO:13) and B (SEQ ID NO:14) (FIGS. 1 and 6) each having 25 nucleotides and synthesized based on the nucleotide sequence determined in Examples 7 and 10, the chromosomal DNA of strain KSM-AP1378 as a template, and a PCR kit (Applied Biosystems) in accordance with a PCR method (one cycle=94° C.×1 min.+55° C.×1 min.+72° C.×3 min., 30 cycles). The resultant DNA fragment was inserted into the SmaI site of a pUC18 plasmid vector, and then subjected to transformation using commercially available E. coli HB101 competent cells. The obtained transformants were replicated onto an LB medium containing 0.4% blue starch (Starch azure, Sigma) and 50 μg/ml of ampicillin, followed by culturing at 37° C. for 12 hours. A single strain which decomposed blue starch and thus formed a halo around its colony was isolated. In a manner similar to that described in Example 3, a plasmid (pAMY100) was prepared from this strain.

Example 12

Recombinant Production of Alkaline Amylopullulanase

A recombinant plasmid mixture was prepared by ligating, using a T4 ligase, a 7.7 kb fragment obtained by cleaving a plasmid pHYPUL (Example 3) containing an alkaline pullulanase domain of the alkaline amylopullulanase and pAMY100 (Example 11) containing the alkaline α-amylase domain of the same gene. E. coli HB101 was transformed with the recombinant plasmid mixture, and each of transformants which emerged was replicated onto an LB medium containing 0.4% blue starch and 50 μg/ml of ampicillin and also onto another LB medium containing 0.8% red pullulan (Kanno, M. and Tomiura, E., Agric. Biol. Chem., 49, 1529 (1985)) and 50 μg/ml of ampicillin, followed by culturing for growth at 37° C. for 12 hours. A strain which formed a halo around its colony on both plates was isolated as a recombinant E. coli capable of producing the alkaline amylopullulanase.

Example 13

Using the recombinant E. coli obtained in Example 12, about 500 μg of a recombinant plasmid was prepared in a manner similar to that described in Example 3. From a restriction enzyme map of the resultant recombinant plasmid, it was found that the plasmid contained a DNA fragment (fragment H) of about 7.0 kb as shown in FIG. 1. This plasmid was named pAP101 (FIG. 2). E. coli HB101 transformed with the plasmid pAP101 was named HB101 (pAP101).

Example 14

A cell-free extract was prepared using E. coli HB101 (pAP101) in a manner similar to that described in Example 4. A control cell-free extract was also prepared using the HB101(pBR322) strain. α-Amylase and pullulanase activities of these extracts were measured. The α-amylase activity was measured by causing a reaction, at 50° C. for 15 minutes, in a reaction mixture containing 50 mM glycine-NaCl—NaOH buffer (pH 10) and soluble starch, and the resultant reducing sugar was quantitatively determined by the DNS method. The pullulanase activity was measured in a manner similar to that described in Example 4. In both cases, the amount of enzyme which produced a quantity per minute of reducing sugar equivalent to 1 μmol of glucose was taken as 1 unit. As a result, α-amylase and pullulanase activities were detected in a cell-free extract of strain HB101 (pAP101). When the optimum working pHs of α-amylase and pullulanase were measured as described in Example 4, it was found that the maximum α-amylase activity and the maximum pullulanase activity were observed in pH ranges from 8 to 9 and from 9 to 10, respectively.

Example 15

Characterization of Alkaline Amylopullulanase

To 50 mg of an alkaline amylopullulanase enzyme (210 kDa; Japanese Patent Publication (kokoku) No. 6-32613) purified from a culture of Bacillus sp. KSM-AP1378, 0.1 mg of papai (Sigma, 5 U/mg) was added and hydrolysis was allowed to proceed at 30° C. for 2 minutes. Subsequently, the reaction was stopped by the addition of 10 µg of antipain (Furuka). The resulting decomposition product was fractionated using a DEAE 5PW column (7.5 mm×7.5 cm; Tosoh) to obtain protein fragments with 114 kDa and 102 kDa. Measurement of enzymatic activities of these two protein fragments revealed that the 102 kDa protein fragment possessed only alkaline pullulanase activity and the 114 kDa protein fragment possessed only alkaline α-amylase activity. The N-terminus of the amino acid sequence of the 102 kDa protein fragment possessing only pullulanase activity was determined to have the sequence Thr-Val-Pro-Leu-Ala-Leu-Val-Ser-Gly-Glu-Val-Leu-Ser-Asp-Lys-Leu, which agreed perfect y with $1014^{th}$–$1029^{th}$ amino acids deduced from the amino acid sequence described in SEQ ID NO:2. Similarly, the N-terminus of the amino acid sequence of the 114 kDa protein fragment possessing only α-amylase activity was determined to have the sequence Glu-Thr-Gly-Asp-Lys-Arg-Ile-Glu-Phe-Ser-Tyr-Glu-Arg-Pro, which agreed perfectly with $1^{st}$–$14^{th}$ amino acids deduced from the amino acid sequence describe in SEQ ID NO:2. These results also proved that the present gene encodes an alkaline amylopullulanase protein having different active centers, i.e., active centers for pullulanase activity and for α-amylase activity.

Example 16

The recombinant plasmid pAP101 was introduced in B. subtilis ISW1214 and the transformed cells were grown at 31° C. for 60 hours, with shaking, in LB medium containing 15 µg/ml of tetraglycine. The alkaline amylopullulanase was found to be excreted at a level of 60 units per liter, in terms of the alkaline pullulanase activity. The expressed enzymes had pH optima of around 8–9 for the amylase activity and at 9.5 for the pullulanase activity, values close to the pH optima for the respective enzymatic activities of the alkaline amylopullulanase of Bacillus sp. KSM-AP1378. The molecular mass of the expressed amylopullulanase protein was approximately 200–210 kDa by sodium dodecyl sulfate gel electrophoresis, a value close to the enzyme of strain KSM-AP1378.

Reference Example 1

A Bacillus sp. KSM-AP1378 strain which produces alkaline amylopullulanase was inoculated into 10 ml of medium A (Table 1) and subjected to shaking culture at 30° C. for 2 days. Ten (10) ml of the culture was inoculated in 1 liter of the same medium, followed by shaking culture at 30° C. for a further 3 days. Subsequently, cells were centrifugally processed to obtain a crude enzymatic liquid containing alkaline amylopullulanase. This crude enzymatic liquid was purified through various treatments including adsorption onto DEAE cellulose, affinity chromatography on a column of Sepharose-α-cyclodextrin, and gel filtration on a column of Sephacryl S-200 to obtain an electrophoretically homogeneous sample of the enzyme. Using a protein sequencer 476A (Applied Biosystems), the N-terminus of the amino acid sequence of this enzyme was determined to have the sequence Glu-Thr-Gly-Asp-Lys-Arg-Ile-Glu-Phe-Ser-Tyr-Glu-Arg-Pro.

Reference Example 2

The optimum pHs for the α-amylase activity and pullulanase activity of alkaline amylopullulanase obtained in Reference example 1 were determined using a method described in Examples 4 and 14. As a result, the optimum pH for α-amylase activity was observed in the vicinity of pH 8.5, and that for pullulanase activity was observed in the vicinity of pH 9.5.

Industrial Applicability

According to the present invention, it is possible to obtain a gene coding for alkaline amylopullulanase exhibiting the maximum activity in an alkaline pH range as well as a microorganism harboring such gene. Use of the present invention facilitates mass production of alkaline amylopullulanase. Alkaline amylopullulanase is characteristic in that it has different active centers, one for α-amylase and one for pullulanase, in a single protein of the enzyme.

What is claimed is:

1. An isolated DNA fragment encoding an amylopullulanase which exhibits both alkaline pullulanase and alkaline α-amylase activities, which encodes an amino acid sequence of SEQ ID NO:2.

2. An isolated DNA fragment consisting of a nucleotide sequence encoding alkaline pullulanase, wherein said alkaline pullulanase consists of the amino acid sequence of SEQ ID NO:4.

* * * * *